US008182557B2

(12) United States Patent
Argyropoulos

(10) Patent No.: US 8,182,557 B2
(45) Date of Patent: *May 22, 2012

(54) USE OF LIGNOCELLULOSICS SOLVATED IN IONIC LIQUIDS FOR PRODUCTION OF BIOFUELS

(75) Inventor: Dimitris Argyropoulos, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 701 days.

This patent is subject to a terminal disclaimer.

(21) Appl. No.: 12/026,997

(22) Filed: Feb. 6, 2008

(65) Prior Publication Data

US 2008/0190013 A1  Aug. 14, 2008

Related U.S. Application Data

(60) Provisional application No. 60/888,438, filed on Feb. 6, 2007.

(51) Int. Cl.
*C10L 5/00* (2006.01)
*C10L 1/00* (2006.01)
*D21C 9/00* (2006.01)
*C10G 1/00* (2006.01)

(52) U.S. Cl. .................. 44/605; 44/307; 162/9; 162/50; 162/91; 585/240; 585/242

(58) Field of Classification Search .................. 44/307, 44/605; 162/9, 50, 91–98; 585/240, 242
See application file for complete search history.

(56) References Cited

U.S. PATENT DOCUMENTS

| 1,924,238 A | 8/1933 | Graenacher |
| 1,943,176 A | 1/1934 | Graenacher |
| 3,926,947 A | 12/1975 | Lipska |
| 4,752,579 A | 6/1988 | Arena et al. |
| 5,221,537 A | 6/1993 | Hecht et al. |
| 5,395,455 A | 3/1995 | Scott et al. |
| 5,536,325 A | 7/1996 | Brink |

(Continued)

FOREIGN PATENT DOCUMENTS

DE  10 2005 017 715 A1  10/2006

(Continued)

OTHER PUBLICATIONS

Abbott et al., "O-Acetylation of Cellulose and Monosaccharides Using a Zinc Based Ionic Liquid," *Green Chemistry*, 2005, pp. 705-707, vol. 7, No. 10.
Arnautov et al., "Electrochemical Synthesis of Polyphenylene in a New Ionic Liquid," *Synthetic Metals*, 1997, pp. 295-296, vol. 84.

(Continued)

*Primary Examiner* — Walter D Griffin
*Assistant Examiner* — Vishal Vasisth
(74) *Attorney, Agent, or Firm* — Alston & Bird LLP

(57) ABSTRACT

The present invention provides a method for converting lignocellulosic material into biofuel. In particular embodiments, the method comprises pre-treating lignocellulosic material by dissolving the material in ionic liquids. The pretreated lignocellulosic material can be isolated, such as by precipitation with a regenerating solvent (e.g., water), and be used directly in the formation of biofuel, including undergoing hydrolysis to form sugar and fermentation to form fuel, such as bioethanol. The ionic liquid can be recycled for further use, such as by evaporation of the water introduced during precipitation, and the recycling provides a route to a hemicellulose rich fraction and an ionic liquid of consistent quality and wood dissolution characteristics. The recovered hemicelluloses are of significant utilization potential toward commodity and specialty applications.

24 Claims, 3 Drawing Sheets

U.S. PATENT DOCUMENTS

| | | | |
|---|---|---|---|
| 5,628,830 A | 5/1997 | Brink | |
| 5,916,780 A | 6/1999 | Foody et al. | |
| 6,509,180 B1 | 1/2003 | Verser et al. | |
| 6,824,559 B2 | 11/2004 | Michal | |
| 7,109,005 B2 | 9/2006 | Eroma et al. | |
| 7,309,602 B2 | 12/2007 | David | |
| 2003/0157351 A1* | 8/2003 | Swatloski et al. | 428/478.4 |
| 2005/0288484 A1* | 12/2005 | Holbrey et al. | 528/480 |
| 2007/0161095 A1* | 7/2007 | Gurin | 435/134 |
| 2008/0023162 A1* | 1/2008 | Myllymaki et al. | 162/163 |

FOREIGN PATENT DOCUMENTS

| | | |
|---|---|---|
| DE | 10 2005 017 733 A1 | 10/2006 |
| EP | 1 860 201 | 11/2007 |
| WO | WO 03/029329 | 4/2003 |
| WO | WO 2005/017001 A1 | 2/2005 |
| WO | WO 2005/017252 | 2/2005 |
| WO | WO 2005/023873 A1 | 3/2005 |
| WO | WO 2005/054298 A1 | 6/2005 |
| WO | WO 2005/066374 A1 | 7/2005 |
| WO | WO 2005/098546 A2 | 10/2005 |
| WO | WO 2006/265544 | 10/2006 |
| WO | WO 2007/005388 | 1/2007 |
| WO | WO 2007/112382 | 10/2007 |
| WO | WO 2007/128268 | 11/2007 |
| WO | WO 2007/144282 | 12/2007 |
| WO | WO 2007/147813 | 12/2007 |
| WO | WO 2008/000666 | 1/2008 |
| WO | WO 2008/003643 | 1/2008 |
| WO | WO 2008/019219 A1 | 2/2008 |
| WO | WO 2008/045021 | 4/2008 |

OTHER PUBLICATIONS

Augustine, et al., "Direct Solvents for Cellulose," *Cellilose Sources and Exploitation, Industrial Utilization, Biotechnology and Physico-Chemical Properties*, 1990, pp. 59-65.

Baeza et al., "Wood and Cellulosic Chemistry," 2$^{nd}$ ed., 2001, Marcel Dekker Inc. New York. (Book)

Berger et al., "Alternative Variants of Dissolving Cellulose in New Organic Solvent Systems," *Cellulose Sources and Exploitation. Industrial Utilization, Biotechnology and Physico-Chemical Properties*, 1990, pp. 67-78.

Biswas et al., "Ionic Liquids as Solvents for Biopolmers: Acylation of Starch and Zein Protein," *Carbohydrate Polymers*, 2006, pp. 546-550, vol. 66.

Branco et al., "Preparation and Characterization of New Room Temperature Ionic Liquids," *Chemistry—A European Journal*, 2002, pp. 3671-3677, vol. 8, No. 16.

Chen et al., "Effect of Pressing on the Infrared Spectra of Single Cotton Fibers," *Applied Spectroscopy*, 2002, pp. 646-650, vol. 56, No. 5.

Collier et al., "Elongational Rheology of Polymer Melts and Solutions," *J. Appl Polym Sci*, 1998, pp. 2357-2367, vol. 69.

Collier et al., Rheology of Lyocell Solutions From Different Cellulose Sources, *Journal of Polymers and the Environment*, 2000, pp. 151-154, vol. 8, No. 3.

Deng et al., "Ionic Liquids as a Green Catalytic Reaction Medium for Esterification," *Journal of Molecular Catalysis A: Chemical*, pp. 33-36, vol. 165.

Dupont et al., "Ionic Liquid (Molten Salt) Phase Organometallic Catalysis," *Chem. Rev.*, 2002, pp. 3667-3692, vol. 102.

Eggeman et al., "Process and Economic Analysis of Pretreatment Technologies," *Bioresource Technology*, 2005, pp. 2019-2025, vol. 96.

Firestone et al., "Lyotropic Liquid-Crystalline Gel Formation in a Room-Temperature Ionic Liquid," *Langmuir*, 2002, pp. 7258-7260, vol. 18.

Fort et al., "Use of Ionic Liquids in the Study of Fruit Ripening by High-Resolution $^{13}$C NMR Spectroscopy: 'Green' Solvents Meet Green Bananas," *Chem. Commun.*, 2006, pp. 714-716.

Fort et al., "Can Ionic Liquids Dissolve Wood? Processing and Analysis of Lignocellulosic Materials with 1-*n*-butyl-3-Methylimidazolium Chloride," *Green Chemistry*, 2007, pp. 63-69, vol. 9. http://www.rsc.org/publishing/journals/GC/article.asp?doi=B607614a.

Gonzalez-Benito et al., "FTIR Imaging of the Dissolution of Polymers. 4. Poly(methyl methacrylate) Using a Cosolvent Mixture (Carbon Tetrachloride/Methanol)," *Macromolecules*, 2002, pp. 7361-7367, vol. 35.

Grethlein, "Chemical Breakdown of Cellulosic Materials," *Journal of Applied Chemistry and Biotechnology*, 1978, pp. 296-308, vol. 28, No. 4.

Hang et al., "Enzymatic Production of Soluble Sugars From Corn Husks," *Lebensmittal-Wissenschaft Und Technologie*, 1999, pp. 208-210, vol. 32, No. 4.

Hinterstoisser et al., "Two-Dimensional Step-Scan FTIR: A Tool to Unravel the OH-Valency-Range of the Spectrum of Cellulose I," *Cellulose*, 1999, pp. 251-263, vol. 6.

Honglu et al., "Wood Liquefaction by Ionic Liquids," *Holzforschung*, 2006, pp. 509-512, vol. 60.

Huddleston et al., "Characterization and Comparison of Hydrophilic and Hydrophobic Room Temperature Ionic Liquids Incorporating the Imidazolium Cation," *Green Chemistry*, 2001, pp. 156-164, vol. 3.

Kaar et al., "Using Lime Pretreatment to Facilitate the Enzymatic Hydrolysis of Corn Stover," *Biomass and Bioenergy*, 2000, pp. 189-199, vol. 18.

Kataoka et al., "Changing Cellulose Crystalline Structure in Forming Wood Cell Walls," *Macromolecules*, 1996, pp. 6356-6358, vol. 29.

Kataoka et al., "FT-IR Microscopic analysis of Chaining Cellulose Crystalline Structure During Wood Cell Wall Formation," *Macromolecules*, 1998, pp. 760-764, vol. 31.

Katz et al., "Production of Glucose by Enzymatic Hydrolysis of Cellulose," *Applied Microbiology*, 1968, pp. 419-420, vol. 16, 2.

Kilpeläinen et al., "Dissolution of Wood in Ionic Liquids," *Journal of Agricultural and Food Chemistry*, 2007, pp. 9142-9148, vol. 55.

Kim et al., "Biocatalysis in Ionic Liquids: Markedly Enhanced Enantioselectivity of Lipase," *Organic Letters*, 2001, pp. 1507-1509, vol. 3, No. 10.

Kim et al., "Graphitization of Highly Crystalline Cellulose," *Carbon*, 2001, pp. 1051-1056, vol. 39.

Klemm et al., "Cellulose: Fascinating Biopolymer and Sustainable Raw Material," *Angew. Chem. Int. Ed.*, 2005, pp. 3358-3393, vol. 44.

Kondo, "The Assignment of IR Absorption Bands Due to Free Hydroxyl Groups in Cellulose," *Cellulose*, 1997, pp. 281-292, vol. 4.

Kragl et al., "Enzyme Catalysis in Ionic Liquids," *Current Opinion in Biotechnology*, pp. 565-571, vol. 13.

Law et al., "Solvent-Free Route to Ionic Liquid Precursors Using a Water-Free Microwave Process," *Green Chemistry*, 2002, pp. 328-330, vol. 4.

Leveque et al., "An Improved Preparation of Ionic Liquids by Ultrasound," *Green Chemistry*, 2002, pp. 357-360, vol. 4.

Liu et al., "Enzymatic Hydrolysis of Cellulose Materials Treated With Ionic Liquid [BMIM] CI," *Chinese Science Bulletin*, 2006, pp. 2432-2436, vol. 51, No. 20.

Liu et al.,"Synthesis and Application of Dictionic Ionic Liquids," *Journal of Chemical Technology and Biotechnology*, 2006, pp. 401-405, 2006, vol. 81, No. 3.

Mabee et al., "Updates on Softwood-to-Ethanol Process Development," *Appl. Biochem. Biotechnol.*, 2006, pp. 55-70, vol. 129-132.

Macosko, *Rheology, Principles, Measurements and Applications, Wiley-VCH*, 1994 (Book).

Mosier et al., "Features of Promising Technologies for Pretreatment Lignocellulosic Biomass," *Bioresource Technology*, 2005, pp. 673-686, vol. 96.

Namboodiri et al., "An Improved Preparation of 1,3-Dialkylimidazolium Tetrafluoroborate Ionic Liquids Using Microwave," *Tetrahedron Letters*, 2002, pp. 5381-5383, vol. 43.

Paillet et al., "New Biodegradable Films from Exploded Wood Solutions," *Journal of Applied Polymer Science*, 1990, pp. 427-433, vol. 40.

Patel et al., "Crystallization Kinetics During Polymer Processing—Analysis of Available Approaches for Process Modeling," *Polym. Eng. Sci.*, 1991, pp. 730-738, vol. 31, No. 10.

Patel et al., "Dynamics and Structure Development During High-Speed Melt Spinning of Nylon 6. II. Mathematical Modeling," *J. Appl. Polym. Sci.*, 1991, pp. 1671-1682, vol. 42.

Petrovan et al., "Rheology of Cellulosic N-Methylmorpholine Oxide Monohydrate Solutions," *Journal of Applied Polymer Science*, 2000, pp. 1369-1377, vol. 77.

Petrovan et al., "Rheology of Cellulosic N-Methylmorpholine Oxide Monohydrate Solutions of Different Degree of Polymerization," *Journal of Applied Polymer Science*, 2001, pp. 396-405, vol. 79.

Petrovan et al., "Elongational and Shear Rheology of Cellulosic and Lignocellulosic Solutions in N-Methylmorpholine Oxide Monohydrate," *Cell Chem. Technol.*, 2001, pp. 89-102, vol. 35, Nos. 1-2.

Phillips et al., "Regenerated Silk Fiber Wet Spinning From an Ionic Liquid Solution," *J. Mater. Chem.*, 2005, pp. 4206-4208, vol. 15.

Ragauskas et al., "The Path Forward for Biofuels and Biomaterials," *Science*, 2006, pp. 484-489, vol. 311.

Rogers et al., "Ionic Liquids-Solvents of the Future?," *Science*, 2003, pp. 792-793, vol. 302.

Romanoschi et al., "Rheological Properties of Kenaf Lyocell Solutions," *Kenaf Properties, Processing and Products*, 1999, pp. 225-244.

Sarymsakov et al., "Study of Partial O-Alkylation of Cotton Cellulose," *Chemistry of Natural Compound*, 1997, pp. 337-339, vol. 33, No. 3.

Seddon, "Ionic Liquids for Clean Technology," *Journal of Chemical Technology and Biotechnology*, 1997, pp. 351-356, vol. 68, No. 4.

Sheldon, "Catalytic Reactions in Ionic Liquids," *Chem. Commun.*, 2001, pp. 2399-2407, vol. 23.

Sun et al., "Hydrolysis of Lignocellulosic Materials for Ethanol Production: A Review," *Bioresource Technology*, 2002, pp. 1-11, vol. 83, No. 1.

Swatloski et al., "Dissolution of Cellulose With Ionic Liquid," *Journal of the American Chemical Society*, 2002, pp. 4974-4975. vol. 124.

Tashpulatov et al., "Enzymatic Production of Glucose Syrups From Cellulose-Containing Plant Wastes," *Chemistry of Natural Compounds*, 1997, pp. 273-275, vol. 33, No. 3.

Treiber, "Trends in the Viscose and Dissolving Pulp Technology," *Cellulose Sources and Exploitation. Industrial Utilization, Biotechnology and Physico-Chemical Properties*, 1990, pp. 163-168.

Turner et al., "Production of Bioactive Cellulose Films Reconstituted from Ionic Liquids," *Biomacromolecules*, 2004, pp. 1379-1384, vol. 5.

Turner et al., "Ionic Liquid-Reconstituted Cellulose Composites as Solid Support Matrices for Biocatalyst Immobilization," *Biomacromolecules*, 2005, pp. 2497-2502, vol. 6.

Vygodskii et al., "Ionic Liquids as Novel Reaction Media for the Synthesis of Condensation Polymers," *Macromolecular Rapid Communications*, pp. 676-680, vol. 23, No. 12.

Wasserscheid et al., "Ionic Liquids-New 'Solutions' for Transition Metal Catalysis," *Angew.Chem., Int. ed.*, 2000, pp. 3772-3789, vol. 39.

Welton, "Room Temperature Ionic Liquids. Solvents for Synthesis and Catalysis," *Chem. Rev.*, 1999, pp. 2071-2083, vol. 99.

Wilke et al., "Raw Materials Evaluation and Process Development Studies for Conversion of Biomass to Sugars and Ethanol," *Biotechnology and Bioengineering*, 1981, pp. 163-183, vol. 23.

Wu et al., "Homogeneous Acetylation of Cellulose in a New Ionic Liquid," *Biomacromolecules*, 2004, pp. 266-268, vol. 5.

Wyman et al., "Coordinated Development of Leading Biomass Pretreatment Technologies," *Bioresource Technology*, 2005, pp. 1959-1966, vol. 96.

Xie et al., "Ionic Liquids as novel Solvents for the Dissolution and Blending of Wool Keratin Fibers," *Green Chem.*, 2005, pp. 606-608, vol. 7.

Xie et al., "Chitin and Chitosan Dissolved in Ionic Liquids as Reversible Sorbents of $CO_2$," *Green Chem.* 2006, pp. 630-633, vol. 8.

Xie et al., "Thorough Chemical Modification of Wood-Based Lignocellulosic Materials in Ionic Liquids," *Biomacromolecules*, 2007, pp. 3740-3748, vol. 8.

Zhang et al., "Novel Properties of Ionic Liquids in Selective Sulfur Removal From Fuels at Room Temperature," *Green Chemistry*, 2002, pp. 376-379, vol. 4.

Zhang et al., "1-Allyl-3methylimidazolium Chloride Room Temperature Ionic Liquid: A New an Powerful Nonderivatizing Solvent for Cellulose," *Macromolecules*, 2005, p. 8272, vol. 38, No. 20.

Ziabicki, *Fundamentals of Fiber Formation. The Science of Fiber Spinning and Drawing*, John Wiley & Sons. 1976 (Book).

Zhu et al., "Dissolution of Cellulose with Ionic Liquids and Its Application: A Mini-Review," *Green Chem.*, 2006, pp. 325-327, vol. 8.

Abstract "Novozymes Working with Chinese on Ethanol From Cellulose," *Focus on Catalysts*, 2006, p. 4, vol. 2006, No. 8.

Alcañiz-Monge et al., "Development of New Carbon Honeycomb Structures From Cellulose and Pitch," *Carbon*, 2002, pp. 541-550, vol. 40.

Byrne, "Carbonization of Wood for Advanced Materials Applications," *Carbon*, 1997, pp. 259-266, vol. 35, No. 2.

Kadla et al., "Lignin-Based Caron Fibers for Composite Fiber Applications," *Carbon*, 2002, pp. 2913-2920, vol. 40.

Kumar et al., "Effect of Reactive Atmosphere and Maximum Heat Treatment Temperature on Characteristics of Pyrolyzed Rayon Cloth," *Carbon*, 1997, pp. 703-706, vol. 35, No. 5.

Mohan et al., "Pyrolysis of Wood/Biomass for Bio-Oil: A Critical Review," *Energy & Fuels*, 2006, pp. 848-889, vol. 20.

Mortimer et al., "The Formation of Structure in the Spinning and Coagulation of Lyocell Fibers," *Cellulose Chemistry and Technology*, 1996, pp. 117-132, vol. 30.

Mortimer et al., "The Influence of Physical Process Parameters on the Structure Formation of Lyocell Fibers," *Cellulose Chemistry and Technology*, 1996, pp. 251-266, vol. 30.

Nimlos et al., "Enhancement of 1,2-Dehydration of Alcohols by alkali Cations and Protons: A Model for Dehydration of Carbohydrates," *Journal of Analytical and Applied Pyrolysis*, 2003, pp. 3-27, vol. 66.

Pastor et al., "Preparation of Activated Carbon Cloths From Viscous Rayon. Part I. Carbonization Procedures," *Carbon*, 1999, pp. 1275-1283, vol. 37.

Plaisantin et al., "Conversion of Cellulose Fibers Into Carbon Fibers: A Study of the Mechanical Properties and Correlation With Chemical Structure," *Composites Science and Technology*, 2001, pp. 2063-2068, vol. 61.

Rabinovich, "Ethanol Production From Materials Containing Cellulose: The Potential of Russian Research and Development," *Applied Chemistry and Microbiology*, 2006, pp. 1-26, vol. 42, No. 1.

Rodriguez-Reinoso et al., "Preparation of Activated Carbon cloths from Viscous Rayon Part III. Effect of Carbonization on the $CO_2$ Activation," *Carbon*, 2000, pp. 397-406, vol. 38.

Sheldrake et al., "Dicationic Molten Salts (Ionic Liquids) as Re-Usable Media for the Controlled Pyrolysis of Cellulose to Anhydrosugars," *Green Chemistry*, 2007, pp. 1044-1046, vol. 9.

Viswanathan et al., "Preparation of Biopolymer Fibers by Electrospinning From Room Temperature Ionic Liquids," *Biomacromolecules*, 2006, pp. 415-418, vol. 7.

Yue et al., "Preparation of Fibrous Porous Materials by chemical Activation 1. $ZnCl_2$ Activation of Polymer-Coated Fibers," *Carbon*, 2002, pp. 1181-1191, vol. 40.

Barthel et al., "Acylation and Carbanilation of Cellulose in Ionic Liquids," *The Royal Society of Chemistry/Green Chem*, 2006, pp. 301-306, vol. 8.

Liebert et al., "Interaction of Ionic Liquids with Polysaccharides 5. Solvents and Reaction Media for the Modification of Cellulose," *BioResources*, 2008, pp. 576-601, vol. 3, No. 2.

Liu et al., "Preparation of Sugarcane Bagasse Cellulosie Phthalate Using an Ionic Liquid as Reaction Medium," *Carbohydrate Polymers*, 2007, pp. 17-25, vol. 68.

Murugesan et al., "Ionic Liquid-Derived Blood-Compatible Composite Membranes for Kidney Dialysis," *J. Biomed. Mater. Res. Part B: Appl. Biomater/InterScience*, 2005, pp. 298-304, vol. 79b.

Schlufter et al., "Efficient Homogeneous Chemical Modification of Bacterial Cellulose in the Ionic Liquid 1-*N*-Butyl-3-Methylimidazolium Chloride," *Macromolecular Rapid Communications/InterScience*, 2006, pp. 1670-1676, vol. 27.

* cited by examiner

USE OF LIGNOCELLULOSICS SOLVATED IN IONIC LIQUIDS FOR PRODUCTION OF BIOFUELS

CROSS-REFERENCE TO RELATED APPLICATIONS

The present application claims priority to U.S. Provisional Patent Application No. 60/888,438, filed Feb. 6, 2007, which is incorporated herein by reference in its entirety.

FIELD OF THE INVENTION

The present invention is directed to methods for converting lignocellulosic material to biofuel. In particular, the invention is directed to methods for solvating lignocellulosic materials in ionic liquids for later use in enzymatic conversion to biofuels.

BACKGROUND

Biomass is an increasingly popular starting material for production of a variety of materials. Ever growing energy demands and environmental concerns have particularly prompted much toward work developing convenient and efficient pathways for converting biomass to biofuels, valuable chemicals, and biomaterials.

Wood is the most abundant lignocellulosic resource on the planet. Although wood has long been used as raw materials for building, fuel, and various products, its use for converting to biofuel and producing valuable chemicals and biomaterials has only recently been considered in light of development of bioengineering and catalytic chemistry.

The complex structure of wood makes it insoluble in common molecular solvents, and preliminary chemical or physical treatment is thus necessary for further applications. Such preliminary treatments, especially chemical treatment, are generally undesirable because of the need to use or release environmental unfriendly chemicals. For example, NaOH and NaSH typically must be used to delignify wood in the kraft pulping manufacturing technology, which is the most popular method used in the paper industry.

For the traditional conversion of wood into composite-materials, wood flour is used or heterogeneous chemical modification is performed. Performing these processes is plagued by feedstock-degradation, as well as the unavoidable consumption of large amounts of energy and expensive chemicals. The traditional method to obtain biodegradable plastic and composites is heterogeneous graft modification, which has been disclosed in U.S. Pat. Nos. 5,424,382, 5,741,875, 5,852,069, and 6,013,774. These methods suffer drawbacks such as low efficiency and utilization of hazardous chemicals.

Lignin is a vastly under-utilized natural polymer. Commercial lignin is currently produced as a co-product of the paper industry, separated from trees by a chemical pulping process. Lignosulfonates (also called lignin sulfonates and sulfite lignins) are products of sulfite pulping. Kraft lignins (also called sulfate lignins) are obtained from the Kraft pulping process. Other delignification technologies use an organic solvent or a high pressure steam treatment to remove lignins from plants. Because lignins are very complex natural polymers with many random couplings, the exact chemical structure is not known, and the physical and chemical properties of lignin can differ depending on the extraction technology and the plant material from which it is extracted. For example, lignosulfonates are hydrophilic and Kraft lignins are hydrophobic. Lignin is typically used as a stabilizer (e.g. an antioxidant) for plastics and rubber, as well as in the formulation of dispersants, adhesives, and surfactants. Lignin or lignin derivatives have also been used in the production of fully biodegradable lignin-based composites.

Ionic liquids have recently received much attention as "green" (environmentally friendly), designable solvents, which are favorable in light of the growing realization of the need to protect the environment. Ionic liquids represent a new way of thinking with regard to solvents. The field is experiencing rapid growth, and offers a starting point for science, industry, and business to cooperate in the formation of a new paradigm of green chemistry and sustainable industry.

Ionic liquids offer a range of significant improvements upon conventional solvents, and also exhibit greater ability than water for solubilizing organic compounds. The unique structure of ionic liquids compared to traditional molecular solvents provides for many unique solubilization characteristics. For example, a range of ionic liquids applicable for the dissolution of cellulose are disclosed in U.S. Pat. No. 6,824,559. Furthermore, ionic liquids have shown good solubility characteristics for monomers or polymers and have been used to reconstitute advanced composites materials, as disclosed in International Publication WO 2005/098546.

Ethanol, also known as grain alcohol, is presently made primarily from the starches and sugars in kernels of field corn. However, starches and sugars constitute only a small portion of plant matter generally. It has heretofore been impossible to employ starches to produce ethanol for biofuel use due to the limitation of available agricultural crops and excessive associated cost. Thus, the ability to commercially produce biofuels, such as bioethanol, is limited by the availability of a low cost, sustainable, and renewable feedstock. As forest resources are sustainably available on an annual basis, lignocellulosics offer an attractive feedstock; as previously noted, the economical and efficient use of such has heretofore been very limited.

Processing of lignocellulosics to ethanol consists of four major unit operations: pretreatment, hydrolysis, fermentation, and product separation/purification. Pretreatment is one of the most important operations for practical cellulose conversion processes, and is a key technical barrier to using cellulosic feedstocks for bioconversion. Pretreatment is required to alter the structure of cellulosic biomass to make cellulose more accessible to the enzymes that convert the carbohydrate polymers into fermentable sugars. An effective pretreatment will disrupt the physical and chemical barriers posed by cell walls, as well as cellulose crystallinity, so that hydrolytic enzymes can access the biomass macrostructure. The low accessibility of enzymes into untreated lignocellulosic matrices is the key hurdle to the commercial success of converting cellulosic biomass to biofuel.

Pretreatment has been viewed as one of the most expensive processing steps in cellulosic biomass-to-fermentable sugar conversion and has a major influence on the cost of most other operations. Effective pretreatment can significantly reduce the use of expensive enzymes. Moreover, pretreatment can strongly influence downstream costs by determining fermentation toxicity, enzymatic hydrolysis rates, enzyme loadings, mixing power, product concentrations, product purification, waste treatment demands, power generation, and other process variables. Of course, the pretreatment operation itself must be low in cost and energy consumption and avoid high consumption of expensive chemicals and feedstock degradation. Thus, there still remains a need in the art for methods of making a greater quantity of biomass readily available for efficient, low-cost conversion to biofuels.

SUMMARY OF THE INVENTION

The present invention provides a pretreatment technique in the preparation of biofuels comprising the dissolution of woody, ligninic, cellulosic, or lignocellulosic materials in ionic liquid media. The pretreatment comprises dissolving the lignocellulosic materials and precipitation of the solvated materials by addition of an appropriate regenerating solvent (e.g., water or other polar solvent). The invention is particularly characterized in that the solvation of the lignocellulosics in the ionic liquid places the lignocellulosics in a state such that they can be rapidly penetrated and hydrolyzed with hydrolytic cellulolytic enzymes, releasing glucose as the source of sugar for the production of ethanol. Thus, the invention provides an efficient, economical, environmentally friendly technique for pre-treating and converting lignocellulosics into biofuels.

The present invention solves the previously limiting problem in the conversion of lignocellulosics into biofuel: the low availability of sugar components in the raw material. According to the present invention, lignocellulosic materials can be treated using environmentally friendly ionic liquids at low temperatures to easily and efficiently transform the lignocellulosics into a solvated form where they can be utilized in known conversion processes to form sugars (such conversion being in excess of 50% of the theoretical maximum yield). The produced sugars can be easily fermented and the produced ethanol separated by distillation.

In one aspect, the present invention is directed to a method of converting lignocellulosic materials (such as woody biomass) into biofuel. In specific embodiments, the method comprises pre-treating the lignocellulosic material by dissolving it in ionic liquid. Such pretreatment is particularly beneficial in that is efficiently makes the material available for further treatment in the efficient conversion to biofuel. In further embodiments, the method can further comprise precipitating the pretreated lignocellulosic material from the ionic liquid. Preferably, the precipitation step comprising adding a polar solvent to the ionic liquid comprising the lignocellulosic material. The thus pretreated lignocellulosic material can then be used in known processes for producing biofuel, such as ethanol.

In certain embodiments, the method can utilize specific parameters. For example, the dissolving step can comprise mixing while heating at a temperature of about 50° C. to about 150° C. Further, it can be useful for the dissolving to be carried out in the substantial absence of particular materials, such as water and/or a nitrogen-containing base. Although a great variety of lignocellulosic materials can be used, the invention is particularly useful in that it allows for the complete dissolution of wood, making this vast resource available for the production of biofuel. It can be useful for the wood to be in a specific state prior to introduction into the ionic liquid. For example, the wood can be in the form of ball-milled wood powder, sawdust, thermomechanical pulp (TMP) fibers, wood chips, and combinations thereof.

Various types of ionic liquids can be used in the invention. Non-limiting specific examples of useful ionic liquids include materials formed of a cation and an anion, wherein the cation is selected from the group consisting of imidazoles, pyrazoles, thiazoles, isothiazoles, azathiozoles, oxothiazoles, oxazines, oxazolines, oxazaboroles, dithiozoles, triazoles, delenozoles, oxaphospholes, pyrroles, boroles, furans, thiophenes, phospholes, pentazoles, indoles, indolines, oxazoles, isoxazoles, isotetrazoles, tetrazoles, benzofurans, dibenzofurans, benzothiophenes, dibenzothiophenes, thiadiazoles, pyridines, pyrimidines, pyrazines, pyridazines, piperazines, piperidines, morpholones, pyrans, annolines, phthalazines, quinazolines, guanidiniums, quinxalines, choline-based analogues, derivatives thereof, and combinations thereof, and wherein the anion is selected from the group consisting of halogens, phosphates, alkylphosphates, alkenylphosphates, $BF_4^-$, $PF_6^-$, $AsF_6^-$, $NO_3^-$, $N(CN)_2^-$, $N(SO_3CF_3)_2^-$, amino acids, substituted or unsubstituted carboranes, perchlorates, pseudohalogens, metal chloride-based Lewis acids, $C_{1-6}$ carboxylates, and combinations thereof.

The invention is also characterized by the ability to recycle the ionic liquid for multiple pre-treatment cycles. In certain embodiments, recycling can comprise removing the regenerating solvent from the ionic liquid, such as by evaporation and the use of hygroscopic materials.

After pretreatment of the lignocellulosic material, it is in a form suitable for further treatment to form a biofuel. For example, the regenerated lignocellulosic material can be isolated from the ionic liquid and converted into a sugar, such as glucose. Such conversion can be carried out by various methods, such as enzymatic hydrolysis. The formed sugars are suitable for use in know methods, such as microbial conversion, to form biofuels. For example, the sugar can be contacted with ethanol forming bacteria.

In another aspect, the invention also provides an intermediate material that is useful in various conversion methods. In certain embodiments, the material comprises a regenerated lignocellulosic material. The regenerated lignocellulosic material is unique in that it has a basic physical structure that is at least about 50% amorphous, which is surprising since the regenerated lignocellulosic material is a lignocellulosic material that, in its native state, has a basic physical structure that is less than 50% amorphous. In one embodiment, the regenerated lignocellulosic material comprises amorphous wood.

In other embodiments, the invention provides methods for the preparation of highly porous, reactive lignocellulosic substrates. In specific embodiments, the method comprises dissolving a lignocellulosic material in an ionic liquid to form a solution, and precipitating the dissolved lignocellulosic material from the ionic liquid to form the highly porous, reactive lignocellulosic substrate.

In still another aspect, the invention provides methods of isolating certain fractions from dissolved lignocellulosic materials. In certain embodiments, the invention provides a method for isolating hemicellulose from a lignocellulosic material. In a particular embodiment, the method comprises: (a) dissolving the lignocellulosic material in an ionic liquid; (b) regenerating the lignocellulosic material having a reduced hemicellulose content; (c) separating the regenerated lignocellulose material from the ionic liquid to provide a recycled ionic liquid; and (d) isolating hemicellulose from the recycled ionic liquid.

BRIEF DESCRIPTION OF THE DRAWINGS

Figure 1B:
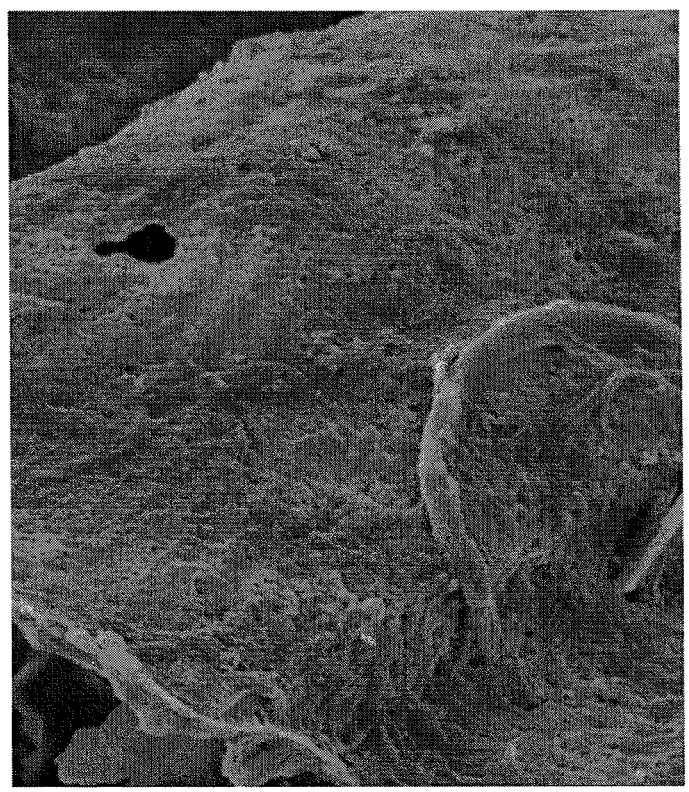
Figure 1A:
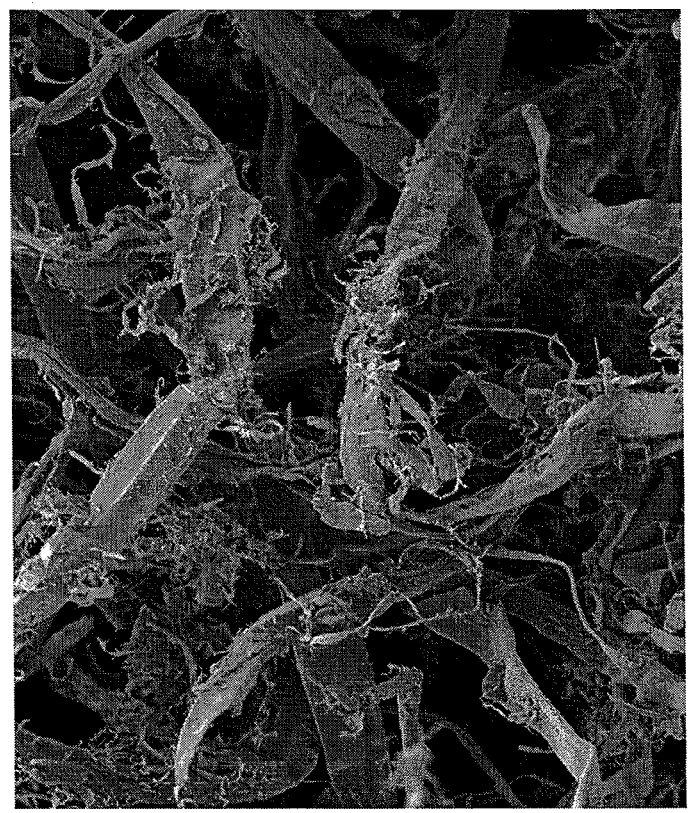
Figure 2:
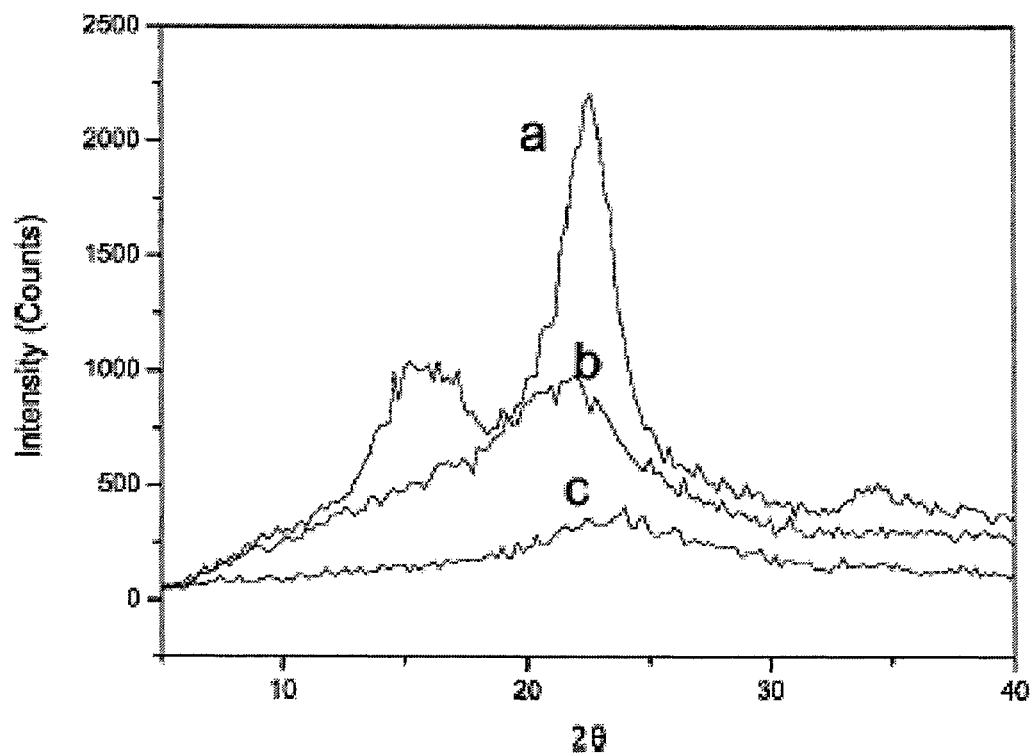
Figure 3:
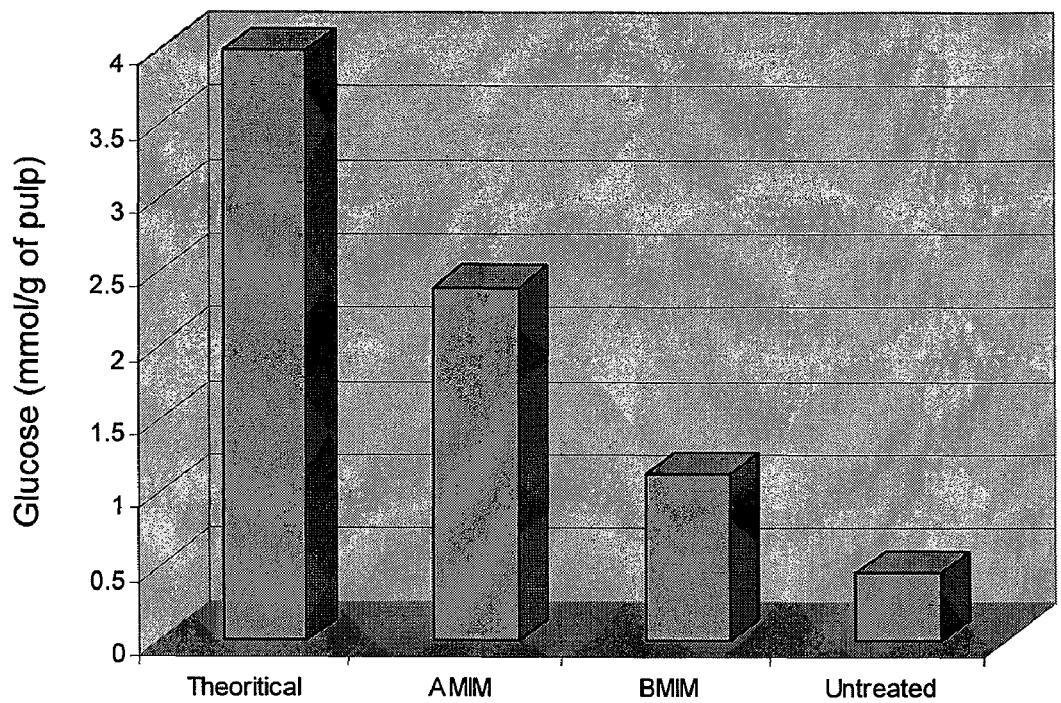
Figure 4:
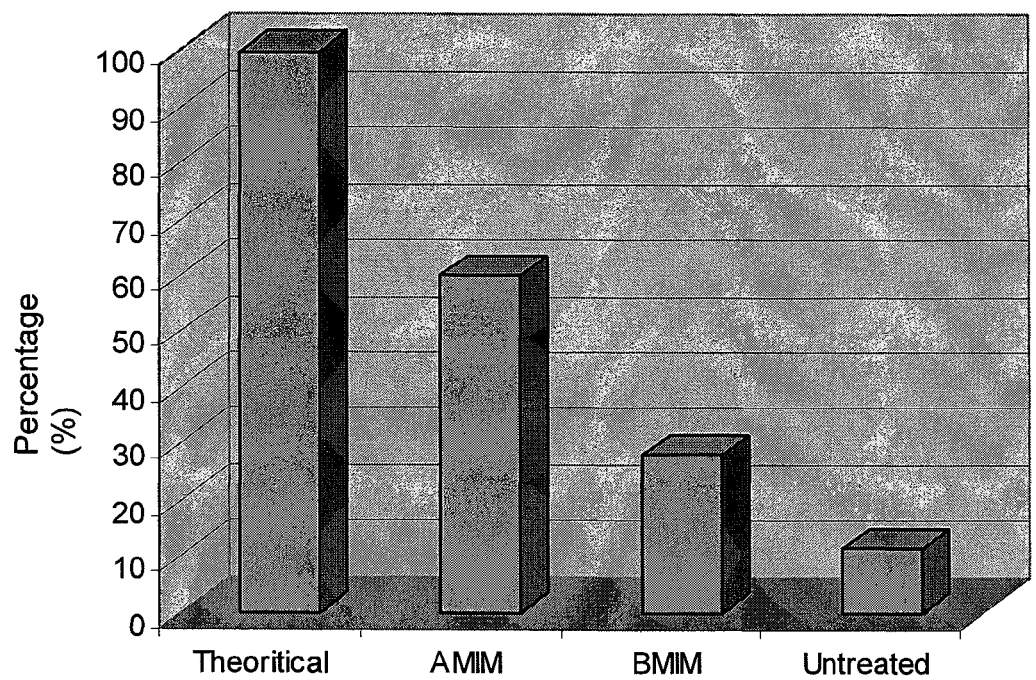
Figure 5:
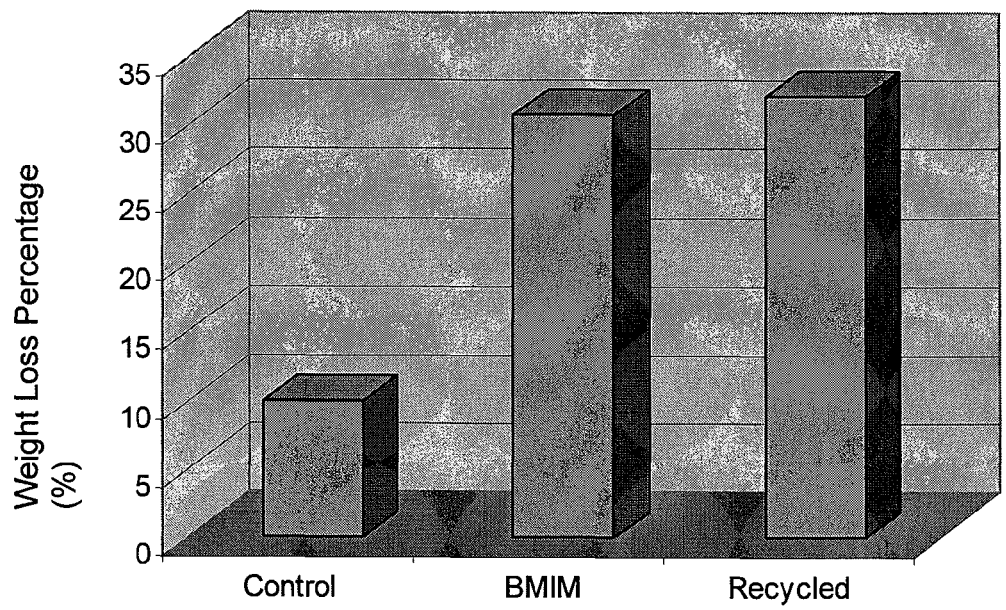

Having thus described the invention in general terms, reference will now be made to the accompanying drawings, which are not necessarily drawn to scale, and wherein:

FIG. 1a is photomicrograph of spruce sawdust showing its basic fibrous structure prior to dissolution in ionic liquid;

FIG. 1b is a photomicrograph of the spruce sawdust from FIG. 1a after dissolution in ionic liquid and regeneration;

FIG. 2 is the X-ray spectra of spruce sawdust undissolved, dissolved in ionic liquid, and regenerated from ionic liquid;

FIG. 3 is a graph illustrating the amount of glucose released during enzymatic hydrolysis of untreated spruce wood, regenerated spruce wood from ionic liquid, and the theoretical yield of glucose from spruce wood in units of mmol/g of pulp processed;

FIG. 4 is a graph illustrating the amount of glucose released during enzymatic hydrolysis of untreated spruce wood, regenerated spruce wood from ionic liquid, as a percentage of the theoretical yield of glucose from spruce wood; and FIG. 5 is a graph illustrating the actual percentage weight loss of three wood samples after being exposed to a standard cellulase enzymatic treatment, with the first sample being untreated softwood, the second sample being the same softwood after being dissolved and regenerated in freshly prepared 1-butyl-3-methyl-imidazolium chloride ("Bmim"), and the third sample being the same softwood after being dissolved and regenerated in recycled 1-butyl-3-methyl-imidazolium chloride ("Recycled").

DETAILED DESCRIPTION

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present invention provides methods for the production of biofuels that overcome the previous limitations in the art. Particularly, the invention provides a pretreatment technique that allows for the use of lignocellulosic materials in the production of biofuels. The pretreatment technique is characterized by the dissolution of the lignocellulosic materials using ionic liquids. The lignocellulosic materials can be effectively and efficiently solvated at low temperatures and subsequently re-precipitated in a regenerating solvent. The solvated lignocellulosic material allows hydrolytic enzymes to rapidly penetrate and hydrolyze the materials in complete presence of the lignin.

The inventive method is particularly beneficial since it typically avoids the production of by-products, such as furfurals and aldehydes, found in the acid treatment technologies that are currently used to dissolve cellulosic materials. Thus, the present invention provides a final yield that exceeds the known processes. Moreover, the method of the present invention provides a significant reduction in feedstock pretreatments costs (on the order of at least 50%) over current hydrolysis methods, such as dilute acid treatment and ammonia fiber explosion. The inventive method has the added benefit of being environmentally friendly as the only materials used (in addition to the feedstock) are ionic liquids (which can be recycled for multiple dissolution processes) and water. Further, since the lignocellulosics are dissolved rather than chemically reacted, the pretreatment liquor can be recovered without significant recovery costs.

The pretreatment process of the present invention provides a number features and advantages. In particular, the inventive methods do not require high heat and pressure operations to dissolve the lignocellulosics. This offers tremendous gains in operational energy savings, as well as reduced installation and maintenance costs. The inventive pretreatment technique also offers an effective elimination of cellulose crystallinity which is thought to accelerate the bioconversion rate. Milder pH conditions also increases enzyme activity in the biofuel preparation stages, and the higher bioconversion rates translate to reduction in production costs. The chemicals used in the pretreatment are recoverable (except those absorbed to the lignocellulosic materials) and environmentally friendly. Further, the pretreatment causes less corrosion problem and less equipment installation costs compared to the dilute acid methods. The novel process is also compatible with current industrial practices with minimal capital investment requirements. The new technology can be widely applied to various biomass materials, especially wood and "ligninic" (i. e., lignin-containing) resources that are difficult to exploit for biofuel conversion.

Ionic Liquids

Generally, ionic liquids can be defined as compounds that are comprised entirely of ions and are liquids at temperatures of less than about 100° C., preferably less than about 85° C. Materials useful as ionic liquids according to the present invention also have a liquid range of up to about 300° C., which allows for good kinetic control. Such ionic liquids are excellent solvents for a wide range of inorganic, organic, and polymeric materials (high solubility generally meaning only small reactor volumes are necessitated and process intensification is provided). Preferentially, the ionic liquids can exhibit Brønsted, Lewis, and Franklin acidity, as well as superacidity, enabling many catalytic processes. They have no effective vapor pressure, are both hydrophilic and hydrophobic systems (further enhancing their industrial application), and are thermally stable up to about 200° C., preferably about 250° C., and more preferably about 300° C. Ionic liquids offer a wide variety of possible solvents allowing for process optimization (there are over a million ($10^6$) simple ionic liquids, and over a trillion ($10^{18}$) ionic liquid combinations). Ionic liquids are further beneficial in that they are relatively inexpensive (particularly in light of their facile recycling potential), easy to prepare, and commercially available.

As used in the present invention, ionic liquids generally comprise one or more anions and one or more cations. In preferred embodiments, the ionic liquids comprise organic cations created by derivatizing one or more compounds to include substituents, such as alkyl, alkenyl, alkynyl, alkoxy, alkenoxy, alkynoxy, a variety of aromatics, such as (substituted or unsubstituted) phenyl, (substituted or unsubstituted) benzyl, (substituted or unsubstituted) phenoxy, and (substituted or unsubstituted) benzoxy, and a variety of heterocyclic aromatics having one, two, or three heteroatoms in the ring portion thereof, said heterocyclics being substituted or unsubstituted. The derivatized compounds include, but are not limited to, imidazoles, pyrazoles, thiazoles, isothiazoles, azathiozoles, oxothiazoles, oxazines, oxazolines, oxazaboroles, dithiozoles, triazoles, delenozoles, oxaphospholes, pyrroles, boroles, furans, thiophenes, phospholes, pentazoles, indoles, indolines, oxazoles, isoxazoles, isotetrazoles, tetrazoles, benzofurans, dibenzofurans, benzothiophenes, dibenzothiophenes, thiadiazoles, pyridines, pyrimidines, pyrazines, pyridazines, piperazines, piperidines, morpholones, pyrans, annolines, phthalazines, quinazolines, guanidiniums, quinxalines, choline-based analogues, and combinations thereof. The basic cation structure can be singly or multiply substituted or unsubstituted.

The anionic portion of the ionic liquid can comprise an inorganic moiety, an organic moiety, or combinations thereof. In preferred embodiments, the anionic portion comprises one or more moieties selected from halogens, phosphates, alkylphosphates, alkenylphosphates, bis(trifluoromethylsulfonyl)imide ($NTf_2$), $BF_4^-$, $PF_6^-$, $AsF_6^-$, $NO_3^-$, $N(CN)_2^-$, N(SO₃CF₃)₂⁻, amino acids, substituted or unsubstituted carboranes, perchlorates, pseudohalogens such as thiocyanate and cyanate, metal chloride-based Lewis acids (e.g., zinc chlorides and aluminum chlorides), or $C_{1-6}$ carboxylates. Pseudohalides are monovalent and have properties similar to those of halides (see, Schriver et al., Inorganic Chemistry, W. H. Freeman & Co., New York (1990) 406-407, which is incorporated herein by reference). Examples of pseudohalides useful according to the invention include cyanides, thiocyanates, cyanates, fulminates, and azides. Exemplary carboxylates that contain 1-6 carbon atoms are formate, acetate, propionate, butyrate, hexanoate, maleate, fumarate, oxalate, lactate, pyruvate and the like. Of course, such list is not intended to be an exhaustive listing of all possible anionic moieties possible according to the invention. Rather, a variety of further anionic moieties are also envisioned and encompassed by the present invention. For example, the invention also encompasses ionic liquids based on alkyl imidazolium or choline chloride anol-aluminum chloride, zinc chloride, indium chloride, and the like. Moreover, various further Lewis acid inorganic salt mixtures may be used (see *Green Chem.* (2005) 7, 705-707, which is incorporated herein by reference).

As noted above, a variety of ionic liquids can be prepared and used according to the present invention. In particular, any combination of the cations and anions noted above could be used. It is only necessary to combine one or more cations (such as those described above) with one or more anions (such as those described above) to form a material that is liquid under the conditions described herein. For example, a cation imidazolium moiety could be combined with an anionic halogen moiety to form a material that is liquid under the requisite conditions (e.g., 1-butyl-3-methyl-imidazolium chloride) and that is formed substantially completely of ionic moieties. Thus, it is clear that the present invention encompasses the use of a great diversity of ionic liquids. Specific, non-limiting examples of ionic liquids for use according to the invention include 1-butyl-3-methyl-imidazolium chloride ("BmimCl"); 1-allyl-3-methyl-imidazolium chloride ("AmimCl"); 1-ethyl-3-methyl-imidazolium chloride; 1-hydrogen-3-methyl-imidazolium chloride; 1-benzyl-3-methyl-imidazolium chloride ("BenzylmimCl"); 1-isopropyl-3-methyl-imidazolium chloride; 1-m-methoxybenzyl-3-methyl-imidazolium chloride ("MethoxyBenzylmimCl"); 1-m-methylbenzyl-3-methyl-imidazolium chloride ("MethylBenzylmimCl"); 1-benzyl-3-methyl-imidazolium chloride, and 1-methyl-3-benzyl-imidazolium dicyanamide ("BenzylmimDca"). These exemplary compounds are illustrated below in Formulas (1) through (6).

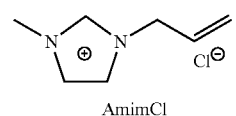

AmimCl
(1)

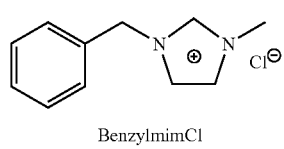

BenzylmimCl
(2)

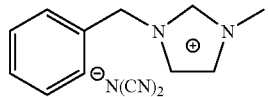

BenzylmimDca
(3)

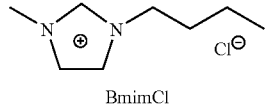

BmimCl
(4)

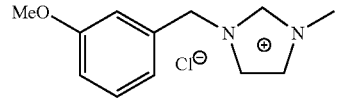

MethoxyBenzylmimCl
(5)

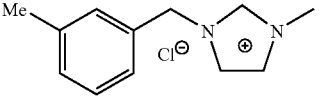

MethylBenzylmimCl
(6)

Exemplary methods for preparing ionic liquids of BenzylmimCl and BenzylmimDca are provided in Examples 1 and 2, respectively.

In still further embodiments, the present invention encompasses the uses of various ionic liquids incorporating phosphates as the anionic portion. Specific, non-limiting examples of such phosphate-containing compounds useful as ionic liquids include: bis[1,3-dimethylimidazolium]methylphosphate—Formula (7); tris[1,3-dimethylimidazolium]phosphate—Formula (8); 1,3-dimethylimidazolium diallylphosphate—Formula (9); 1,2,3-trimethylimidazolium dimethylphosphate—Formula (10); 1-benzyl-3-methylimidazolium dimethylphosphate—Formula (11); 1-vinyl-3-methylimidazolium dimethylphosphate—Formula (12); 1,3-dimethylimidazolium dimethylphosphate—Formula (13); 1,2,3-trimethylimidazolium methylhydrogenphosphate—Formula (14); and 1-allyl-3-methylimidazolium dimethylphosphate—Formula (15). Related compounds can be prepared by transesterification of the phosphate anion with an alcohol such as, allyl alcohol.

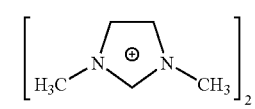

MePO₄²⁻
(7)

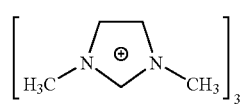

PO₄³⁻
(8)

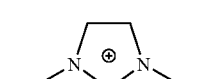

(Allyl)₂PO₄⁻
(9)

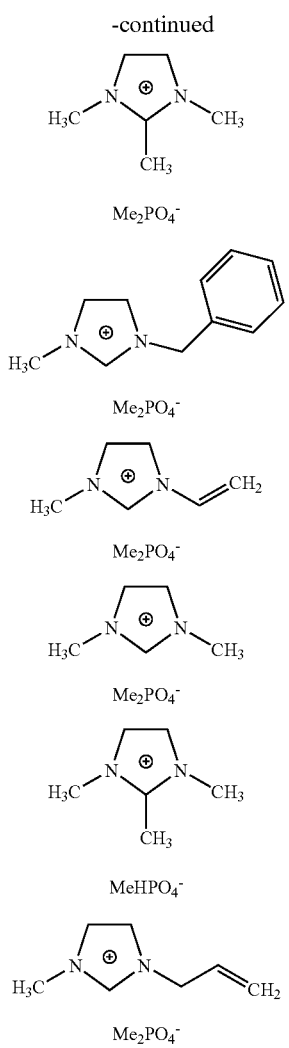

Phosphate-containing ionic liquids can be particularly useful according to the present invention. Such compounds are typically relatively easy to prepare by synthesis methods, they readily dissolve woody lignocellulosic materials, and ionic liquids based on such materials exhibit viscosities in ranges making them particularly easy to use without the need for excessive heating. For example, when compared to halide-based ionic liquids (especially chloride-based ionic liquids), phosphate-based ionic liquids, such as those noted above, exhibit viscosities in the range of three to five times less than the viscosities typically exhibited by the halide-based ionic liquids.

Although the ionic liquids exemplified above in Formulas (1) through (15) use imidazole cation, the present invention should not be limited only to the use of imidazole cationic moieties. Rather, as previously noted, the imidazole series of ionic liquids are only representative of the types of ionic liquids that can be used according to the invention. For example, in Formulas (1) though (15), the imidazole cation could be replaced with a pyridinium cation. Thus, the invention clearly also encompasses liquids formed of compounds as illustrated in Formulas (1) through (15) but wherein the cationic portion is a pyridinium cation. In other words, the invention particularly encompasses pyridinium chlorides and pyridinium phosphates. In specific embodiments, the ionic liquids useful according to the invention encompass allyl-methyl-pyridinium chloride, ethyl-methyl-pyridinium chloride, methyl-pyridinium chloride, benzyl-methyl-pyridinium chloride, isopropy-1-methyl pyridinium chloride, 1-m-methoxybenzyl-methyl-pyridinium chloride, 1-m-methylbenzyl-methyl-pyridinium chloride, or benzyl-methyl-pyridinium chloride. Likewise, it is clear that multiple pyridinium phosphate ionic liquids could be used based on the compounds of Formulas (7) through (15) wherein the imidazolium cation is substituted with a pyridinium cation. Based on this disclosure, it is also clear how to arrive at still further ionic liquids for use according to the invention. For example, useful ionic liquids could be based on an imidazolium cation or a pyridinium cation paired with any suitable anion as described above. Likewise, useful ionic liquids could be based on a chloride anion or a phosphate anion paired with any suitable cation as described above.

As previously pointed out, the ionic liquids used according to the invention can encompass one or more cations combined with one or more anions. In specific embodiments, the invention comprises the use of cation liquids formed of dicationic compounds. Dicationic materials can exhibit increased thermal stability and are thus useful in embodiments where it may be desirable to carry out the dissolution of lignocellulosic materials at increased temperature. Dicationic ionic liquids can be prepared using any combination of cations and anions, such as those described above. For example, imidazoles and pyridines could be used in preparing dicationic ionic liquids in a similar manner as the ionic liquids described above using only a single cationic moiety.

In certain embodiments, the invention encompasses dicationic liquids having the structure provided below in Formulas (16) and (17)

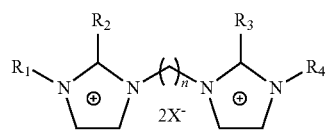

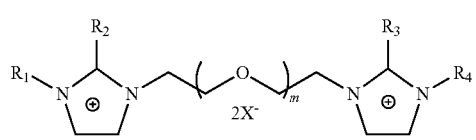

wherein n is an integer from 4 to 10; m is an integer from 1 to 4; X is a cationic moiety selected from the group consisting of Cl, Br, I, NTf$_2$, (R)$_2$PO$_4$, and RHPO$_4$; and R, R$_1$, R$_2$, R$_3$, and R$_4$ are independently selected from the group consisting of H, C$_{1-6}$ alkyl, C$_{1-6}$ alkenyl, and C$_{1-6}$ alkynyl. One specific example of a dicationic ionic liquid according to Formula (16) that is useful according to the present invention is the compound shown below in Formula (18).

(18)

In further embodiments, the invention also encompasses dicationic liquids having the structure provided below in Formulas (19) and (20)

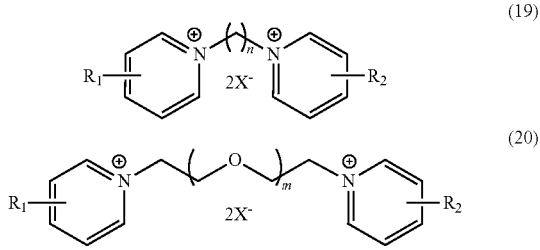

wherein n is an integer from 4 to 10; m is an integer from 1 to 4; X is a cationic moiety selected from the group consisting of Cl, Br, I, bis(trifluoromethylsulfonyl)imide (NTf$_2$), (R)$_2$PO$_4$, and RHPO$_4$; and R, R$_1$, and R$_2$ are independently selected from the group consisting of H, C$_{1-6}$ alkyl, C$_{1-6}$ alkenyl, and C$_{1-6}$ alkynyl. Dicationic compounds useful as ionic liquids according to the present invention can be prepared through synthesis methods known in the art. See, for example, *J. Chem. Technol Biotechnol.*, 81 (2006), p. 401-405, which is incorporated herein by reference in its entirety.

The invention also encompasses the use of various mixtures of ionic liquids. In fact, ionic liquid mixtures can be useful for providing ionic liquids having customized properties, such as viscosity. For example, BenzylmimCl is a relatively viscous ionic liquid; however, it viscosity can be significantly reduced by mixing with AmimCl. The viscosity of the ionic liquid mixture can thus be adjusted by varying the ratio between the more viscous component and the less viscous component.

Of course, in light of the above disclosure around suitable cationic moieties and suitable anionic moieties, the present invention also encompasses the many ionic liquids that can be prepared through suitable combinations of the disclosed cationic moieties and anionic moieties. Various further ionic liquids useful according to the invention are disclosed in U.S. Pat. No. 6,824,599, which is incorporated herein by reference.

Aromatic group-containing ionic liquids are particularly useful according to the invention. While not wishing to be bound by theory, it is believed that π-π interactions among the aromatic groups in lignin may account for the conformationally stable supermolecular structure of lignin. Thus, cationic moieties with an electron-rich aromatic π-system can create stronger interactions for polymers capable of undergoing π-π and n-π interactions. In particular, the aromatic character of the imidazolium ring of an ionic liquid cation offers potential π-π interactions with many aromatic moieties. Phenyl-containing ionic liquids provide particularly good solubilization of woody materials, as well as lignocellulosic materials generally.

Ionic liquids for use according to the invention can be synthesized according to the literature. Preferably, the ionic liquids are dried (e.g., at 100° C.) in a vacuum oven over a period of time, such as about 48 hours, prior to use. In one embodiment, the ionic liquid is formed of a material that is solid (e.g., crystalline) at ambient conditions but is liquid at increased temperature (such as greater than about 30° C., greater than about 40° C., greater than about 50° C., greater than about 75° C., greater than about 85° C., or greater than about 100° C.). Generally, the crystalline material can be placed in an appropriated container and heated to dissolution. See, for example, *Ionic Liquids in Synthesis*, Wasserscheid, P. and Weldon, T. (Eds.), Wiley Pub., which is incorporated herein by reference. Of course, the ionic liquid can also comprise a material that is liquid at ambient conditions (e.g., at a temperature around 20-25° C.). In particular, the present invention can encompass ionic liquids that are liquid at a temperature of about −10° C. to about 150° C., about 0° C. to about 150° C., or about 15° C. to about 150° C. Further, various ionic liquids are provided in prepared form, such as BASIONICS™ (available from BASF), which are imidazolium-based ionic liquids that are available in standard, acidic, basic, liquid-at-room-temperature, and low-viscosity forms.

Cellulosics and Lignocellulosics

Cellulose is a polysaccharide formed of 1,4-linked glucose units and is the primary structural component found in plants. Cellulose is the most abundant organic chemical on earth, and there is an estimated annual biosphere production of approximately 90×10$^9$ metric tons of the material. When measured in energy terms, the amount of carbon synthesized by plants is equivalent to about ten times the currently estimated global energy consumption.

Lignin is a compound that is most commonly derived from wood and is an integral part of the cell walls of plants. It is a three-dimensional amorphous natural polymer containing phenylpropane units that are tri- or tetra-substituted with hydroxyl groups and methoxyl groups. Lignin makes up about one-quarter to one-third of the dry mass of wood and generally lacks a defined primary structure. Lignocellulose is primarily a combination of cellulose, lignin, and hemicellulose. It is generally thought to be practically impossible to dissolve wood in its native form because the three-dimensional lignin network binds the whole wood architecture together. For example, in papermaking, the lignin network is fragmented under alkaline conditions, and cellulose is harvested as cellulose fibers. The insolubility of wood in common solvents has severely hampered the development of new methods for the efficient utilization of wood and its components. As described below, however, though the use of ionic liquids, it is possible to achieve complete dissolution of lignocellulosics, including wood in its native form.

Accordingly, the invention is particularly characterized in that a wide variety of cellulosics and lignocellulosics can be used as the biomass. For example, the biomass used in the invention can be derived from both herbaceous and woody sources. Non-limiting examples of herbaceous biomass sources useful according to the invention include tobacco, corn, corn stovers, corn residues, cornhusks, sugarcane bagasse, castor oil plant, rapeseed plant, soybean plant, cereal straw, grain processing by-products, bamboo, bamboo pulp, bamboo sawdust, and energy grasses, such as switchgrass, miscanthus, and reed canary grass.

The invention is particularly characterized by it efficacy toward the dissolution of different woody lignocellulosic materials. A variety of hardwoods and softwoods can be used in the invention in a multitude of different forms, such as chips, shreds, fibers, sawdust, and other physical forms. In a preferred embodiment, wood for use in the invention is in the form of dust or powder, such as ball milled powder.

The pretreatment process of the invention is particularly beneficial in that it has shown to be effective for use with softwoods. This is significant since the hydrolysis of softwood species is typically very low compared with hardwood species and other lignocellulosic materials when most of the current technologies are applied. Therefore, the method of the present invention provides a potential technique for biofuel production using softwood species, which are generally more abundant, and faster growing, than most hardwood species.

Softwood is a generic term typically used in reference to wood from conifers (i.e., needle-bearing trees from the order Pinales). Softwood-producing trees include pine, spruce, cedar, fir, larch, douglas-fir, hemlock, cypress, redwood and yew. Conversely, the term hardwood is typically used in reference to wood from broad-leaved or angiosperm trees. The terms "softwood" and "hardwood" do not necessarily describe the actual hardness of the wood. While, on average, hardwood is of higher density and hardness than softwood, there is considerable variation in actual wood hardness in both groups, and some softwood trees can actually produce wood that is harder than wood from hardwood trees. One feature separating hardwoods from softwoods is the presence of pores, or vessels, in hardwood trees, which are absent in softwood trees. On a microscopic level, softwood contains two types of cells, longitudinal wood fibers (or tracheids) and transverse ray cells. In softwood, water transport within the tree is via the tracheids rather than the pores of hardwoods.

Still further, various lignocellulosics generally regarded as "waste" materials can be used according to the present invention. For example, materials that have heretofore been discarded or thought of little value, such as corn stover, rice straw, paper sludge, and waste papers, can all be used as a lignocellulosic starting material according to the present invention. Particularly, it is possible to use various grades of paper and pulp, including recycled paper, which include various amounts of lignins, recycled pulp, bleached paper or pulp, semi-bleached paper or pulp, and unbleached paper or pulp. Such papers and pulps can be of various lignin contents and origins.

The present invention may be described herein in terms of lignocellulosic materials; however, such term does not necessarily exclude the use of materials that may more specifically be defined as cellulosic materials or ligninic materials. Rather, the term lignocellulosic is intended to broadly refer to biomass that may be primarily formed of cellulose, lignin, or lignocellulose. Thus, as used herein, lignocellulosic can mean materials derived from woody sources, grassy sources, and other plant sources generally. Specifically, lignocellulosic can mean a material comprised partly or mainly of lignin, cellulose, or lignocellulose.

Pretreatment Process

The pretreatment process of the invention comprises solvating lignocellulosics using ionic liquids, as described herein. The dissolution of the lignocellulosic material can be carried out under a variety of conditions. For example, in specific embodiments, the ionic liquid used in the pretreatment process is in the substantial absence of water (i.e., is substantially free of water). In other embodiments, the ionic liquid used in the pretreatment process is in the substantial absence of a nitrogen-containing base (i.e., is substantially free of any nitrogen-containing base). The phrases "substantial absence" and "substantially free" are used synonymously to mean that the ionic liquid comprises less than about 5% by weight water and/or less than about 5% by weight of a nitrogen-containing base. In one embodiment, the ionic liquid comprises less than about 5% by weight water. In another embodiment, the ionic liquid comprises less than about 5% by weight of a nitrogen-containing base. In yet another embodiment, the ionic liquid comprises less that about 5% by weight of water and nitrogen-containing base combined. In particularly preferred embodiments, the ionic liquid comprises less than about 1% by weight water and/or nitrogen-containing base. In specific embodiments, the ionic liquid is completely free of water, is completely free of nitrogen-containing base, or is completely free of both water and a nitrogen-containing base.

The lignocellulosics can be added to the ionic liquid media and the admixture can be agitated in any suitable reaction vessel until dissolution is complete. Heat can be provided to the mixture in certain embodiments, such as in an ultrasonic bath, an oil bath or, by microwave irradiation. The ionic liquid is preferably molten at a temperature of less than about 150° C., more preferably less than about 100° C., more preferably less than about 85° C. Such temperatures are likewise sufficient to dissolve the lignocellulosics in the ionic liquid. Preferably, pretreatment is carried out such that the reaction mixture of the ionic liquid and the lignocellulosic material is maintained under an inert atmosphere. In one embodiment, the dissolution is carried out under an argon atmosphere. In another embodiment, the dissolution is carried out under a nitrogen atmosphere. This is particularly useful to avoid introduction of water into the ionic liquid. Reaction according to the invention can be carried out, however, with the reaction vessel open to the atmosphere so long as relative humidity is low so as to avoid the presence of excess water in the air around the reaction vessel.

The pretreatment is useful to dissolve the lignocellulosics, thus providing them in a form more readily subject to further action, such as enzymatic activity. Complete dissolution of lignocellulosic materials, including wood in its native form, can be achieved by simply mixing the lignocellulosic material with the ionic liquid. Preferably, the mixing is carried out at a temperature suitable to maintain the liquid state of the ionic liquid. In certain embodiments, the mixing is carried out at a temperature of about 50° C. to about 150° C., about 60° C. to about 140° C., about 70° C. to about 130° C., or about 80° C. to about 120° C. Although increasing temperature tends to reduce the time to total dissolution, it is possible to obtain total dissolution at even ambient temperature. For example, when wood sawdust is gently homogenized with AmimCl in a mortar and the sample is subsequently transferred into a test tube (under argon), the mixture slowly turns to liquid (complete dissolution) over time. Temperature can also be influenced by the ionic liquid composition. Ionic liquids with lower viscosities can be used at lower temperatures, while ionic liquids with higher viscosities can require higher temperatures.

Preferably, the reaction parameters for the pretreatment are coordinated so that complete dissolution is achieved in a desired time. For example, in certain embodiments, pretreatment is carried out such that complete dissolution is achieved in a time of less than about 48 hours, less than about 36 hours, less than about 24 hours, less than about 18 hours, less than about 12 hours, less than about 10 hours, less than about 8 hours, less than about 6 hours, less than about 4 hours, less than about 2 hours, or less than about 1 hour. Of course, the time to complete dissolution can vary according to the various embodiments of the invention and be related to factors, such as the nature of the ionic liquid, the charge of lignocellulosic material in the ionic liquid, the applied temperature, and the degree of material diminution.

Dissolution can also be facilitated through application of mechanical stirring using any known stirring means. Achieving complete dissolution of even wood fibers has been demonstrated using a hot stage optical microscopy investigation of Norway spruce sawdust sample in AmimCl. Optical photomicrographic analysis of wood dissolution as a function of time at a temperature of 120° C. indicated that, after four hours, any visible fibrous material was completely dissolved by the ionic liquid.

Depending upon the nature of the lignocellulosic material, it may be further useful for dissolution to be carried out with further considerations. For example, the dissolution rate of wood can be dependant upon the particle size of the wood. It is believed that the complex and compact structure of the wood cell wall between the lignin, cellulose, and hemicellulose would essentially inhibit the diffusion of the ionic liquid into its interior, resulting in only a partial dissolution of wood chips. Solubility of lignocellulosics, particularly wood in its native form, can be increased through sample preparation. Solubilization efficiency of lignocellulosic materials in ionic liquids can be defined, in certain embodiments, as follows (shown on a decreasing solubilization basis): ball-milled wood powder>sawdust>thermomechanical pulp fibers>wood chips. For example, the dissolution of fine sawdust (Norway spruce, particle size=0.1-2 mm) in ionic liquid has been shown to take place within a few hours, even under ambient conditions.

In specific embodiments, the present invention is particularly characterized by the achievement of complete dissolution of the lignocellulosic material in the ionic liquid to form a true solution. By contrast, it is possible to form simply a well dispersed gelatinous, highly swollen mixture of a lignocellulosic material and ionic liquid. Such mixtures do not necessarily provide the lignocellulosic material in a form that facilitates the later beneficial uses of the completely solvated lignocellulosic material, such as the formation of biofuels described below. Through use of the specific pretreatment parameters provided herein, and particularly application of continuous mechanical agitation during dissolution, it is possible to form a true solution, particularly a wood solution (i.e., wood completely solubilized in ionic liquid).

According to the present invention, the pretreatment process allows for preparation of solutions of lignocellulosics in ionic liquids. The solvated lignocellulosics are in a state making them particularly open to further modification, such as being acted upon by various enzymes. The solubility limit of lignocellulosics in the ionic liquids can vary depending upon the choice of ionic liquid, the choice of lignocellulosic material, and the physical state of the lignocellulosic material. In certain embodiments, it is possible according to the invention to form solutions having a lignocellulosic concentration of up to about 20% by weight, based upon the overall weight of the solution. In other embodiments, it is possible to form solutions having lignocellulosic concentrations of up to about 18% by weight, up to about 16% by weight, up to about 14% by weight, up to about 12% by weight, up to about 10% by weight, up to about 9% by weight, up to about 8% by weight, up to about 7% by weight, up to about 6% by weight, or up to about 5% by weight, based on the overall weight of the solution. In specific embodiments, the solution comprises about 2% to about 20% by weight, about 2% to about 16% by weight, about 2% to about 12% by weight, about 2% to about 10% by weight, about 2% to about 8% by weight, or about 5% to about 8% by weight of the lignocellulosic material. Table 1 provides the dissolution behavior of various wood-based lignocellulosic materials in different imidazolium-based ionic liquids.

TABLE 1

| Sample | Ionic Liquid | Wood Sample Form | Conditions | Wt. % |
| --- | --- | --- | --- | --- |
| 1 | BmimCl | Wood chips | 130° C., 15 h | ** |
| 2 | AmimCl | Ball-milled Southern pine powder | 80° C., 8 h | 8% |
| 3 | AmimCl | Norway spruce sawdust | 110° C., 8 h | 8% |
| 4 | AmimCl | Norway spruce sawdust | 80° C., 24 h | 5% |
| 5 | BmimCl | Norway spruce sawdust | 110° C., 8 h | 8% |
| 6 | AmimCl | Norway spruce TMP | 130° C., 8 h | 7% |
| 7 | BmimCl | Norway spruce TMP | 130° C., 8 h | 7% |
| 8 | AmimCl | Southern pine TMP | 110° C., 8 h | 2% |
| 9 | AmimCl | Southern pine TMP | 130° C., 8 h | 5% |
| 10 | BmimCl | Southern pine TMP | 130° C., 8 h | 5% |
| 11 | BenzylmimCl | Southern pine TMP | 130° C., 8 h | 5% |
| 12 | BenzylmimCl | Norway spruce TMP | 130° C., 8 h | 5% |
| 13 | MethoxyBenzylmimCl | Southern pine TMP | 130° C., 8 h | 5% |
| 14 | MethoxyBenzylmimCl | Southern pine TMP | 130° C., 8 h | 2% |
| 15 | BenzylmimDca | Southern pine TMP | 130° C., 8 h | 2% |

** Sample showed only partial solubility

The pretreatment process of the invention is particularly useful in light of the complex nature of lignocellulosics, as previously noted. The highly crystalline character of cellulose in wood is driven by a set of regular intermolecular and intramolecular hydrogen-bonding interactions that when coupled with the three-dimensional network character of lignin and its possible covalent linkages with the carbohydrates are primarily responsible for the complex and compact structure of wood. For example, π-π interactions among the aromatic groups in lignin have been suggested as accounting for the conformationally stable supermolecular structure of lignin. Ionic liquids have a more complex solvent behavior compared with traditional solvents, and that complex solvent behavior can include π-π, n-π, hydrogen bonding, dipolar, and ionic/charge-charge types of interactions between the ionic liquids and their solutes. It has been reported that although the Bmim cation does not have the analogous electron aromatic system, the chloride anion (with nonbonding electrons), in combination with the Bmim cation, forms an ionic liquid that exhibits the ability to interact with π-systems of certain molecules. For example, the active chloride ions in ionic liquids, such as BmimCl and other ionic liquids described herein, may disrupt the hydrogen-bonding interactions present in wood, allowing it to diffuse into the interior of the wood.

After dissolution of the lignocellulosic material, the solvated material can be isolated (regenerated) from the mixture. In one embodiment, such isolation is through precipitation with a suitable regenerating solvent. The regenerating solvent according to the invention can comprise any polar solvent, such as water or an alcohol. In specific embodiments, it is preferred to use polar solvents having a boiling point that is less than the boiling point of water. Precipitation is typically spontaneous upon the addition of the regenerating solvent, and the precipitated material can be physically separated from the mixture, such as by evaporation. In one embodiment, regeneration under rapid mechanical stirring results in the formation of a fully amorphous material. This is illustrated in FIG. 1a and FIG. 1b. FIG. 1a is a photomicrograph of spruce sawdust before dissolution in ionic liquid (AmimCl), and the fibrous nature of the material is clearly evident. FIG. 1b, however, is a photomicrograph of the same sawdust after dissolution in ionic liquid and regeneration by precipitation in water. As seen in FIG. 1b, the fibrous nature of the material is completely gone and the material has been restructured to be highly amorphous. This is further illustrated by the X-ray spectra of the regenerated material illustrated in FIG. 2 because the X-ray diffraction signals from the crystalline regions of spruce sawdust have disappeared after the dissolution-regeneration process. In FIG. 2, peak (a) is the diffraction peak of untreated spruce sawdust, peak (b) is the diffraction peak of spruce sawdust after being regenerated from solution in AmimCl using water as the nonsolvent, and peak (c) is the diffraction peak of 8% by weight spruce sawdust dissolved in BmimCl.

In light of the above, it is clear that the process of the invention is useful for preparing a regenerated lignocellulosic material having a basic structure that is different from the basic structure of the native material. For example, prior to dissolving in ionic liquid, wood is in the form of multiple fibers, as illustrated in FIG. 1a. However, the regenerated wood is completely amorphous in nature (FIG. 1b) and is void of the original fibrous nature. Accordingly, the method of the invention is useful for forming a regenerated lignocellulosic material having a basic structure that is at least about 50% amorphous, at least about 75% amorphous, at least about 80% amorphous, at least about 85% amorphous, at least about 90% amorphous, at least about 95% amorphous, at least about 97% amorphous, at least about 98% amorphous, or at least about 99% amorphous.

The present invention thus also provides an amorphous lignocellulosic material. The amorphous lignocellulosic material has an amorphous basic structure, as described, and it thus differs from the native form of the lignocellulosic material. Particularly, the native form of the lignocellulosic material has a defined structure that is less than 50% amorphous. More particularly, the native form of the lignocellulosic material has a defined structure that is less than 40% amorphous, less than 30% amorphous, less than 20% amorphous, or less than 10% amorphous. For example, woods are fibrous in their native form. This is illustrated in FIG. 1a, which shows a native form of spruce wood that is substantially completely fibrous. However, FIG. 1b shows the same spruce wood in the regenerated form according to the invention. As seen therein, the wood is substantially completely amorphous (i.e., there is no identifiable fiber structure present). In one embodiment, the invention provides amorphous wood. Such wood can be described as being substantially amorphous (i.e., at least about 90% of the basic structure is in the amorphous state) or as being completely amorphous (i.e., at least about 99% of the basic structure is in the amorphous state).

The nature (and useful characteristics) of the regenerated lignocellulosic material arises from the breakdown of the natural structure of the material on a microscopic level. This is particularly evident in woody materials, which are significantly fibrous in their native state. The regenerated wood of the present invention, however, is significantly altered such that the wood is no longer fibrous in nature but is significantly completely amorphous. In this new state, the material is physically made more susceptible to outside actions by "opening-up" the physical structure.

In certain embodiments, the invention provides regenerated wood in a form such that at least about 75% of the fibers present in the wood in its native state are no longer present. In further embodiments, the regenerated wood is in a form such that at least about 80%, at least about 85%, at least about 90%, at least about 95%, or at least about 99% of the fibers present in the wood in its native state are no longer present. Rather, in the place of the original fibers, is bulky mass of amorphous physical structure.

The disrupted structure of the emerging lignocellulosic material (i.e., the material regenerated from the solution in ionic liquid) represents a new and highly porous, bulky substrate that is easily accessible and highly reactive towards various chemicals, enzymes, and even gases. Since the wood fibers have been dissolved and re-formed to have an expanded surface area, more of the basic wood structure is available to be acted on. The regenerated lignocellulosic material can be provided in a variety of forms making it a very useful commodity for further reactions and for the preparation of various derivatives and new composite materials. Such new materials can now truly be wood-based materials. For example, the regenerated lignocellulosic material can be powdered or provided in a variety of further forms. Thus, the regenerated lignocellulosic material made possible by the present invention, and particularly regenerated wood, is a renewable substrate that can form the basis for a variety of products, including products that now depend on the availability of non-renewable resources.

The amorphous lignocellulosic material provided according to the present invention is particularly characterized by the beneficial increase in surface area since the fibrous structure of the material has been completely changed. The demonstrated, augmented enzymatic reactivity and accessibility of the regenerated lignocellulosic materials is exemplary of its higher surface area. Furthermore, that the amorphous, regenerated lignocellulosic material of the invention is significantly different from the starting lignocellulosic material is evidenced by the reduced crystallinity of the regenerated lignocellulosic material, as described below in relation to FIG. 2.

The data illustrated in FIG. 2 show that spruce sawdust dissolved in AmimCl displays a slight broad amorphous diffraction peak centered around 2θ of 25°, in the absence of the characteristic diffraction pattern of wood cellulose, which usually displays a prominent sharp peak near 15° and 23°. Thus, FIG. 2 demonstrates that the crystallinity of the cellulose in the wood was eliminated with the ionic liquid dissolution-regeneration treatment. Such a transformation is particularly beneficial to allow a greater accessibility for hydrolytic enzymes to rapidly penetrate and hydrolyze the wood. A similar transformation is likewise seen with the lignin content of materials that are solubilized in ionic liquid and regenerated according to the present invention. In particular, the lignin component of the lignocellulosic substrate exhibits an accessibility to enzymatic and chemical transformations that greatly exceeds such accessibility of the material in its native state. These advantages are further described below.

The present invention is further beneficial in that the ionic liquid media in the inventive pretreatment method can be easily recovered and reused. As noted above, after the pretreatment step, the ionic liquid with the dissolved lignocellulosics therein can be mixed with a regenerating solvent to facilitate precipitation of the lignocellulosic materials. After recovery of the precipitated materials, the regenerating solvent can be removed from the ionic liquid by known methods, such as simple evaporation. Preferably suitable drying methods, such as the use of hygroscopic materials (e.g., anhydrous $Na_2SO_4$), are also employed to ensure the ionic liquid to be recovered is substantially free of the regenerating solvent. The recovered ionic liquid can then be reused for multiple future pretreatment steps. For example, the steps of pre-treating the lignocellulosic material by dissolution in the ionic liquid, precipitation and recovery of the solvated lignocellulosics, and recovery of the ionic liquid can be described as encompassing a single pretreatment cycle. In certain embodiments, ionic liquids used according to the present invention can be recovered for use in multiple pretreatment cycles. Preferably, an ionic liquid can be recovered and used in at least 2 pretreatment cycles, at least 3 pretreatment cycles, at least 4 pretreatment cycles, at least 5 pretreatment cycles, at least 6 pretreatment cycles, at least 7 pretreatment cycles, at least 8 pretreatment cycles, at least 9 pretreatment cycles, or at least 10 pretreatment cycles. This provides for great cost savings, as well as being environmentally responsible.

Recycling of the ionic liquid according to the present invention is further beneficial since it has been discovered that such recycling leads to useful fractionation. In specific embodiments, recycling and reusing the ionic liquid in multiple pretreatment cycles causes the ionic liquid to become enriches in hemicelluloses. For example, in one evaluation, the lignin content of regenerated eucalyptus wood was shown to increase with the use of recycled ionic liquid. Specifically, an ionic liquid was obtained and used for multiple cycles in the dissolution of eucalyptus wood, which is known to have a total lignin content of about 20%. The eucalyptus wood sample was dissolved in the ionic liquid and regenerated, such as described above. After the first cycle, the regenerated eucalyptus wood comprises 24% acid insoluble lignin and 7.2% acid soluble lignin for a total lignin content of 31.2%. The recycled ionic liquid was used in a further cycles to dissolve a sample of eucalyptus wood, which was then regenerated and evaluated for lignin content. The results of the evaluation are shown below in Table 2.

TABLE 2

| Cycle | Acid-insoluble lignin | Acid-soluble lignin | Total Lignin | Note |
|---|---|---|---|---|
| 1 | 24% | 7.2% | 31.2 | Regenerated wood after $1^{st}$ cycle |
| 2 | 30% | 7.8% | 37.8 | Regenerated wood after $2^{nd}$ cycle |
| 3 | 29% | 6.8% | 35.8 | Regenerated wood after $3^{rd}$ cycle |
| 4 | 28% | 6.9% | 34.9 | Regenerated wood after $4^{th}$ cycle |
| 5 | 4.9% | 3.4% | 8.3 | Material still dissolved in ionic liquid |

As seen in Table 2, after each cycle, the regenerated wood had a higher total lignin content than the content of native eucalyptus wood, which indicates that the regenerated wood has a reduced carbohydrate content. After cycle five, the material dissolved in the ionic liquid was precipitated out. Upon evaluation, the isolated material was shown to have a total lignin content of 8.3%. This low lignin content indicates that the recycled ionic liquid is enriched in carbohydrate content (e.g., hemicelluloses). Detailed sugar analyses of this fraction were consistent with a xylan and mannan rich biopolymer as anticipated by the presence of glucuronoxylans and glucomannans in such species.

To facilitate enrichment of the recycled ionic liquid in hemicelluloses, it is possible to purify the recycled ionic liquid. For example, the recycled ionic liquid can be combined with a material that is a non-solvent for hemicelluloses (e.g., acetonitrile or tetrahydrofuran). This allows for the hemicelluloses to be precipitated in the non-solvents. Accordingly, the recycled ionic liquid is purified of the fractionated hemicelluloses, which are recovered. Thus, the invention provides a method for isolating hemicelluloses from lignocellulosic materials, including woody and non-woody species.

In one embodiment, the method of isolating hemicelluloses from lignocellulosic materials comprises dissolving the lignocellulosic material in an ionic liquid, regenerating the lignocellulosic material having a reduced hemicellulose content, separating the regenerated lignocellulose material from the ionic liquid to provide a recycled ionic liquid, and isolating hemicelluloses from the recycled ionic liquid. In particular, the step of isolating hemicelluloses from the recycled ionic liquid can comprise precipitating the hemicelluloses from the ionic liquid. This step can further comprise adding to the recycled ionic liquid a solvent in which hemicelluloses are not soluble (i.e., a hemicellulose non-solvent). The precipitated hemicelluloses can be separated from the ionic liquid by methods recognized as suitable for such separations.

BioFuel Formation

The pretreated lignocellulosic material recovered from the pretreatment steps described above can beneficially be used directly in known methods for the preparation of biofuels. As noted above, the pretreated lignocellulosic material, after recovery from the ionic liquid, is in a regenerated form making it more susceptible to further reactions. For example, the pretreated lignocellulosic material can be submitted to an enzymatic hydrolysis using typical conditions normally applied for such a process to convert the regenerated lignocellulosic material into sugars. The type of sugar formed can be varied depending upon the enzymatic and hydrolytic conditions. Typically, glucose is formed for the subsequent conversion into ethanol.

One known method to convert cellulose to glucose relies on acid hydrolysis (see Grethlein, Chemical Breakdown Of Cellulosic Materials, *J. Appl. Chem. Biotechnol.* 28, (1978) 296-308), which uses concentrated or dilute acids. The concentrated acid process uses 72%, by weight, sulfuric acid or 42%, by weight, hydrochloric acid at room temperature to dissolve the cellulose, followed by dilution to 1% acid and heating to 100° C. to 120° C. for up to three hours to convert cellulose oligomers to glucose monomers. The dilute acid process uses 0.5% to 2%, by weight, sulfuric acid at 180° C. to 240° C. for several minutes to several hours. U.S. Pat. Nos. 5,221,537 and 5,536,325 describe a two-step process for the acid hydrolysis of lignocellulosic material to glucose.

As an alternative to acid hydrolysis, cellulose conversion processes have been developed using a treatment comprising enzymatic hydrolysis. A typical treatment by enzymatic hydrolysis is carried out by mixing the substrate and water to achieve a slurry of 5% to 12%, by weight of cellulose, and then adding cellulase enzymes. Typically, the hydrolysis is run for 24 to 150 hours at 50° C. and pH 5. At the end of the hydrolysis, glucose, which is water soluble, is in the liquid while unconverted cellulose, lignin, and other insoluble portions of the substrate remain in suspension. The glucose syrup is recovered by filtering the hydrolysis slurry; some washing of the fiber solids is carried out to increase the yield of glucose.

Further examples of methods for converting the regenerated lignocellulosics into sugars are provided in the following, all of which are incorporated herein by reference: Tashpulatov, Z. T. et al., *Chemistry of Natural Compounds,* 33(7), 1997; Hang, Y. D. et al., *Lebensmittel-Wissenschaft und Technologie,* 32(4), 1999; Katz, M. and Reese, E. T., *Applied Microbiology,* 16(2), 1968; Liu, L. Y., and Chen, H. Z., *Chinese Science Bulletin,* 51(2), 2006; U.S. Pat. Nos. 5,916,780; 4,752,579; and 5,628,830.

The glucose (or other sugars) formed as described above can be used in a typical fermentation process to prepare the biofuel. In other words, the process of the invention can comprise microbially converting the formed sugars into a biofuel, such as by contacting the sugars with bacteria useful for forming the desired biofuel. Again, the final biofuel prepared can be varied depending upon the type of sugar prepared in the hydrolysis step. In one embodiment, the bacteria can be ethanol-forming bacterial. There are several traditional ethanol processes based on fermentation of carbohydrates. In the most typical process, sugars are fermented by yeast to produce ethanol. Carbon dioxide is generated in the process from a fraction of the carbohydrate by the metabolism of the yeast. Yeast typically have a limited ability to utilize sugars other than glucose. While glucose is the major sugar produced from the hydrolysis of the starch from grains, it is not the only sugar produced in carbohydrates generally. The hydrolyzate typically contains glucose, but also large amounts of other sugars such as xylose, which yeast cannot metabolize. Research has been directed to the use of organisms other than yeast which in contrast to yeast, do consume many if not most of the sugars derived from the hydrolysis of biomass. Examples include *Zymomonas* sp. bacteria and *E. coli* bacteria which have been genetically engineered to utilize xylose. Thereby the potential range of substrate sugars which can be converted to ethanol has been increased.

It is generally assumed in the literature on ethanol fermentation that ethanol yield limitation is fixed by the biochemical pathway called the Embden-Myerhof pathway by which ethanol is produced in all of the organisms so far proposed for production of ethanol, including the thermophiles. A great number of bacteria are capable of ethanol formation. Many of these microorganisms generate multiple end products in addition to ethyl alcohol. These include other alcohols (butanol, isopropyl alcohol, 2,3-butanediol), organic acid (acetic acid, formic acid, and lactic acids), polyols (arabitol, glycerol and xylitol), ketones (acetone) or various gases (methane, carbon dioxide, hydrogen). Examples of microbes that are capable of yielding ethanol as the major product (i.e. a minimum of 1 mol ethanol produced per mol of glucose utilized) are *Clostridium sporogenes*, *Clostridium indoli*, *Clostridium sphenoides*, *Clostridium sordelli*, *Zymomonas mobilis*, *Zymomonas mobilis*, *Spirochaeta aurantia*, *Spirochaeta stenostrepta*, *Spirochaeta litoralis*, *Erwinia amylovora*, *Leuconostoc mesenteroides*, *Streptococcus*, and *Sarcina ventriculi*. Specific examples of methods for preparing biofuels from sugars can be found in the following, all of which are incorporated herein by reference: U.S. Pats. Nos. 7,309,602; 7,109,005; and 6,509,180. Prepared biofuel can be isolated through techniques known in the art, such as distillation.

While various pretreatment methods have been tried, it has not heretofore been possible to arrive at an overall method for preparing biofuel from celluloses, and especially lignocelluloses, that is commercially attractive. Even with the most efficient currently known pretreatment processes, the amount of cellulase enzyme required to convert cellulose to glucose is so high as to be cost-prohibitive for ethanol production purposes. The pretreatment method of the present invention, however, overcomes this problem by effectively compromising the complex cellular structure of lignocelluloses, including woody materials, and "opening-up" the structures for effective attack by enzymes to convert the regenerated materials into the appropriate sugars.

In one evaluation of the reactivity of regenerated materials toward cellulolytic enzymes, spruce wood was pretreated via dissolution in ionic liquid and regeneration, as described above. The regenerated material was then submitted to an enzymatic hydrolysis using a method described by Mabee, W., *Appl. Biochem. Biotechnol.* (2006) pp. 129-132, which is incorporated herein by reference. Although not completely optimized, the evaluation showed that about 60% of the theoretical amount of glucose was enzymatically released from the wood when predissolved in AmimCl and regenerated by precipitation in water. By comparison, only 12% of glucose units were released from the untreated control wood sample (spruce wood sawdust). Similar pretreatments in BmimCl were also found to improve the release of glucose units in comparison to untreated wood. This is illustrated in the graph provided in FIG. 3. Said graph shows the amount of glucose released during enzymatic hydrolysis with ionic liquid pretreatment in millimoles per gram of wood and in percentage terms compared with the theoretical maximum for spruce wood.

The recycling of the ionic liquid, as described above, can also provide advantages in the production of biofuels. In specific embodiments, the use of a single ionic liquid for multiple cycles has actually been shown beneficial for improving cellulose hydrolysis during enzymatic treatment. Particularly, the recycled ionic liquid has been shown to provide better hydrolysis than when using a freshly prepared ionic liquid. In one test, softwood treated with a freshly prepared 1-butyl-3-methyl imidazolium chloride ionic liquid exhibited a 28% release of glucose upon enzymatic hydrolysis. However, when the same ionic liquid was recycled and used to pre-treat a second wood sample, the pretreated wood exhibited a 39% release of glucose. In a control experiment (wood without pretreatment), only 12% of cellulose was released upon enzymatic hydrolysis. These findings can be attributed, in part, to the significant amount of hemicelluloses dissolved in the ionic liquid during the treatment. It is believed this causes fractionation and enrichment of the various wood components on subsequent re-precipitation cycles. After a certain number of cycles, it can be beneficial to remove the hemicellulose fractions from the recycled ionic liquid to maintain consistent quality and wood dissolution characteristics of the ionic liquid.

EXPERIMENTAL

The present invention will now be described with specific reference to various examples. The following examples are not intended to be limiting of the invention and are rather provided as exemplary embodiments.

EXAMPLE 1

Preparation of 1-benzyl-3-methyl-imidazolium chloride

The ionic liquid was prepared with benzyl chloride (0.25 mol) and 1-methylimidazole (0.23 mol) using $CH_3CN$ as solvent in a 250 mL three-neck bottle. The mixture was refluxed for 48 hours under an argon atmosphere. After evaporation of the solvent and of the residual benzyl chloride, the pure ionic liquid was obtained. Drying of the materials took place at 120° C. under vacuum by stirring for 24 hours. The product was of a gelatinous nature at room temperature.

EXAMPLE 2

Preparation of 1-methyl-3-benzyl-imidazolium dicyanamide

The ionic liquid was prepared by anion exchange reaction between 1-methyl-3-benzylimidazolium chloride (0.20 mol) and $NaN(CN)_2$ (0.21 mol) using water as the solvent. The homogenous mixture was stirred at room temperature for 12 hours. After evaporation of the water, 50 mL of $CH_2Cl_2$ was added into the residue. The formed NaCl was filtered, and the organic solvent phase was dried with anhydrous MgSO$_4$. After filtration of the MgSO$_4$ and evaporation of the solvent, a yellow liquid ionic liquid was obtained.

EXAMPLE 3

Dissolution of Lignin in 1-Butyl-3-Methyl Imidazolium Chloride

1-Butyl-3-Methyl Imidazolium Chloride (10 g) was charged into a 50 ml dried flask under inert atmosphere (Ar). The temperature of the dissolution process was controlled using an oil bath at 120° C. Dried lignin (Kraft pine, Kraft hardwood, or lignosulfonate) was added into the ionic liquid to form a 10% w/w solution prepared over two hours under mechanical stirring. The dissolution of lignin in ionic liquid results in the formation of a viscous, brown-black solution.

EXAMPLE 4

Pretreatment of Wood With Ionic Liquid

Dissolution in ionic liquids was carried out using sawdust from Norway Spruce, Eucalyptus, Redwood, Douglas Fir, Southern Pine trees, and a variety of tropical hardwoods, as well as banana tree wood. The wood was initially dried under vacuum (~1 mmHg) at 50° C. for 18 hr. A loss of ~5% weight was typically observed for these samples upon drying.

For dissolving each sample, 10 g of 1-allyl-3-methyl ionic liquid was transferred to a flask with a sidearm fitted for inert gas. Wood dust (0.5 g) was added to the surface of the ionic liquid and mechanically stirred at a low speed to homogenize the mixture under a positive pressure of argon gas. When the mixture was thoroughly mixed, the sample was heated in an oil bath, under argon gas, at approximately 85° C. for 18 hrs. After the heating and dissolution process, the homogenized mixture of the wood and ionic liquid was cooled. To this solution water was added (100 mL) in order to precipitate the lignocellulosic material. The precipitate was collected for spectrographic analysis.

The initial and the regenerated spruce wood from the ionic liquids were characterized by X-ray diffraction (as illustrated in FIG. 2). Review of the spectra indicated that the X-ray diffraction spectral peaks typically derived from the crystalline regions of the cellulose were dramatically eliminated after the pretreatment in the ionic liquid. Therefore, it can be concluded that the crystallinity of the cellulose in the wood was virtually eliminated with the ionic liquid pretreatment.

EXAMPLE 5

Enzymatic Hydrolysis of Pretreated Wood

Spruce wood pretreated as described in Example 4 (using Amim ionic liquid and Bmim ionic liquid) was subjected to an enzymatic hydrolysis, using typical conditions normally applied for this process. As a comparative, spruce wood that was not pretreated was subjected to the same hydrolysis treatment. The theoretical yield of glucose from the wood was 4 mmol of glucose per gram of wood (mmol/g). In the sample pretreated according to the invention, a glucose yield of 2.4 mmol/g was achieved meaning approximately 60% of the theoretically possible glucose units were released from the wood pretreated in ionic liquid. In the untreated sample, only 0.45 mmol/g (12% of the theoretical yield) of glucose units were released upon hydrolysis. This is further illustrated in FIG. 3 and FIG. 4.

Additional gains in the glucose yield can be made through use of more optimized conditions, as well as a variety of enzyme cocktails specialized for production of glucose. Generally, different wood species are expected to behave differently during enzymatic hydrolysis, but the difference between the untreated material and that pre-treated with ionic liquid always remains on the order described above.

EXAMPLE 6

Weight Loss as Evidence of Increased Glucose Production

Samples of spruce wood were exposed to a standard cellulase enzymatic treatment to convert the cellulose present in the sample to glucose. One sample was first dissolved and regenerated using freshly prepared 1-butyl-3-methyl-imidazolium chloride (Bmim). A second sample was first dissolved and regenerated using Bmim that was recycled from previous dissolutions. Both Bmim dissolved samples were exposed a cellulase enzymatic treatment, and the percentage weight loss of the sample subjected to the enzymatic treatment was calculated by obtaining the difference between the weight of the material subjected to the enzymatic treatment minus the weight of unconverted cellulose, lignin, and other insoluble portions of the substrate remaining in suspension and dividing by the weight of the material subjected to the enzymatic treatment. As a comparative, an enzymatic treatment was also carried out on a sample of spruce wood that was not subjected to any pretreatment. Pretreatment according to the invention resulted in an approximate three-fold increase in actual percentage weight loss during enzymatic treatment. The percentage weight loss for each sample is illustrated in FIG. 5.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of converting a wood into biofuel comprising:
   (i) pre-treating the wood in its native form by dissolving in ionic liquid to form a solution of dissolved wood in ionic liquid; said dissolving comprises mixing while heating at a temperature of about 50° C. to about 150° C.
   (ii) precipitating the pretreated wood from the ionic liquid to form a regenerated wood; and
   (iii) carrying out one or more further steps to convert the regenerated wood to a biofuel or to a reactant in the direct preparation of a biofuel.

2. The method of claim 1, wherein said dissolving is carried out in the substantial absence of water.

3. The method of claim 2, wherein said dissolving is carried out such that the ionic liquid comprises less than about 1% by weight water.

4. The method of claim 1, wherein said dissolving is carried out in the substantial absence of a nitrogen-containing base.

5. The method of claim 4, wherein said dissolving is carried out such that the ionic liquid comprises less than about 1% by weight of a nitrogen-containing base.

6. The method of claim 1, wherein the ionic liquid comprises a material formed of a cation and an anion, wherein the cation is selected from the group consisting of imidazoles, pyrazoles, thiazoles, isothiazoles, azathiozoles, oxothiazoles, oxazines, oxazolines, oxazaboroles, dithiozoles, triazoles, delenozoles, oxaphospholes, pyrroles, boroles, furans, thiophenes, phospholes, pentazoles, indoles, indolines, oxazoles, isoxazoles, isotetrazoles, tetrazoles, benzofurans, dibenzofurans, benzothiophenes, dibenzothiophenes, thiadiazoles, pyridines, pyrimidines, pyrazines, pyridazines, piperazines, piperidines, morpholones, pyrans, annolines, phthalazines, quinazolines, guanidiniums, quinxalines, choline-based analogues, derivatives thereof, and combinations thereof, and wherein the anion is selected from the group consisting of halogens, phosphates, alkylphosphates, alkenylphosphates, $BF_4^-$, $PF_6^-$, $AsF_6^-$, $NO_3^-$, $N(CN)_2^-$, $N(SO_3CF_3)_2^-$, amino acids, substituted or unsubstituted carboranes, perchlorates, pseudohalogens, metal chloride-based Lewis acids, $C_{1-6}$ carboxylates, and combinations thereof 7. The method of claim 6, wherein the cation is selected from the group consisting of imidazoles and pyridines, and the anion is selected from the group consisting of halogens, phosphates, alkylphosphates, alkenylphosphates, and bis(trifluoromethylsulfonyl)imide.

8. The method of claim 1, wherein the wood, prior to dissolving in the ionic liquid, is in a form selected from the group consisting of ball-milled wood powder, sawdust, thermomechanical pulp fibers, wood chips, and combinations thereof.

9. The method of claim 1, wherein the precipitation step comprises adding a regenerating solvent to the solution.

10. The method of claim 1, wherein the regenerated wood has a basic structure that is at least about 95% amorphous.

11. The method of claim 1, further comprising recycling the ionic liquid after precipitation of the wood.

12. The method of claim 11, wherein said recycling comprising removing the regenerating solvent from the ionic liquid.

13. The method of claim 1, wherein said ionic liquid comprises an ionic liquid that has been recycled from a previous pre-treatment step.

14. The method of claim 1, wherein the one or more further steps comprises isolating the regenerated wood from the ionic liquid and converting the isolated regenerated wood into a sugar.

15. The method of claim 14, wherein said converting step comprises enzymatic hydrolysis in the presence of an amount of lignin present within the wood in its native form.

16. The method of claim 14, further comprising microbially converting the sugar into a biofuel.

17. The method of claim 16, wherein said microbially converting step comprises contacting the sugar with ethanol forming bacteria.

18. The method of claim 1, wherein the biofuel comprises ethanol.

19. The method of claim 1, wherein the reactant comprises glucose.

20. A method for preparing a highly porous, reactive wood substrate, the method comprising:
 (a) dissolving a wood in its native form in an ionic liquid to form a solution; said dissolving comprises mixing while heating at a temperature of about 50° C. to about 150° C. and
 (b) precipitating the dissolved wood from the ionic liquid to form the highly porous, reactive regenerated wood substrate.

21. The method of claim 20, wherein said precipitating step comprises adding a regenerating solvent to the solution.

22. A method for isolating hemicellulose from a wood, said method comprising:
 (a) dissolving the wood in its native form in an ionic liquid; said dissolving comprises mixing while heating at a temperature of about 50° C. to about 150° C.
 (b) regenerating the wood having a reduced hemicellulose content;
 (c) separating the regenerated wood from the ionic liquid to provide a recycled ionic liquid; and
 (d) isolating hemicellulose from the recycled ionic liquid.

23. The method of claim 22, wherein said isolating step comprises precipitating the hemicellulose from the ionic liquid.

24. The method of claim 23, wherein said precipitating comprises adding to the recycled ionic liquid a solvent in which the hemicellulose is not soluble.

* * * * *